(12) United States Patent
Furbush

(10) Patent No.: US 12,419,988 B2
(45) Date of Patent: Sep. 23, 2025

(54) MEDICAL DEVICE, METHOD OF USING AND MAKING THE SAME

(71) Applicant: Syntervention, Inc., Rocky Mount, NC (US)

(72) Inventor: Norman C. Furbush, Elm City, NC (US)

( * ) Notice: Subject to any disclaimer, the term of this patent is extended or adjusted under 35 U.S.C. 154(b) by 132 days.

(21) Appl. No.: 17/063,484

(22) Filed: Oct. 5, 2020

(65) Prior Publication Data

US 2021/0100926 A1 Apr. 8, 2021

Related U.S. Application Data

(60) Provisional application No. 62/909,895, filed on Oct. 3, 2019.

(51) Int. Cl.
| | |
|---|---|
| *A61L 15/42* | (2006.01) |
| *A61L 15/22* | (2006.01) |
| *A61L 15/52* | (2006.01) |
| *A61L 15/54* | (2006.01) |

(52) U.S. Cl.
CPC ............ *A61L 15/425* (2013.01); *A61L 15/22* (2013.01); *A61L 15/52* (2013.01); *A61L 15/54* (2013.01); *A61L 2300/404* (2013.01)

(58) Field of Classification Search
CPC ........ A61L 15/425; A61L 15/22; A61L 15/52; A61L 15/54; A61L 2300/404; A61F 2250/0098; A61F 13/44; A61F 13/05; A61F 13/36; A61M 2205/03
See application file for complete search history.

(56) References Cited

U.S. PATENT DOCUMENTS

| | | | |
|---|---|---|---|
| 727,146 A | 5/1903 | Johnson | |
| D181,367 S | 11/1957 | Moroni | |
| 3,566,871 A * | 3/1971 | Richter | ................ A61L 15/425 604/362 |
| 3,678,933 A | 7/1972 | Moore et al. | |
| 3,949,742 A | 4/1976 | Nowakowski | |
| 3,961,629 A | 6/1976 | Richter et al. | |
| 4,193,405 A | 3/1980 | Abels | |
| D261,936 S | 11/1981 | Sumiyasu | |
| D268,208 S | 3/1983 | Brown et al. | |
| 4,626,251 A | 12/1986 | Shen | |
| D297,461 S | 8/1988 | Inoue et al. | |

(Continued)

FOREIGN PATENT DOCUMENTS

| | | |
|---|---|---|
| EM | EU0091770250001 | 9/2022 |
| EM | EU0091770250002 | 9/2022 |

(Continued)

OTHER PUBLICATIONS

Translation of JP-2013538629-A (Year: 2013).*

(Continued)

*Primary Examiner* — Rachael E Bredefeld
*Assistant Examiner* — Seth R. Brown
(74) *Attorney, Agent, or Firm* — Messner Reeves LLP; Scott J. Hawranek

(57) ABSTRACT

The invention is directed towards a device, method of using and making the same and more particularly to a sterile, biocompatible, fiber free, foam device configured to be used in various different uses, e.g., medical uses, make-up removal uses, and other uses.

21 Claims, 9 Drawing Sheets

(56) References Cited

U.S. PATENT DOCUMENTS

| | | | |
|---|---|---|---|
| D313,651 S | 1/1991 | Michelson et al. | |
| 5,010,902 A | 4/1991 | Rambo et al. | |
| 5,274,874 A | 1/1994 | Cercone et al. | |
| 5,447,505 A | 9/1995 | Valentine et al. | |
| 5,556,391 A | 9/1996 | Cercone et al. | |
| D375,816 S | 11/1996 | Long-Langworthy et al. | |
| 5,584,386 A | 12/1996 | Ahonen | |
| D382,343 S | 8/1997 | Wandell et al. | |
| D389,581 S | 1/1998 | Fein et al. | |
| 6,004,640 A * | 12/1999 | Pisacane | A47L 1/15 15/244.4 |
| D439,982 S | 4/2001 | Ruscitti | |
| 6,613,347 B2 | 9/2003 | Drury | |
| D504,540 S | 4/2005 | Bailey | |
| D637,501 S | 5/2011 | Begin et al. | |
| D658,769 S | 5/2012 | Moser et al. | |
| D709,205 S | 7/2014 | Ehninger et al. | |
| D723,701 S | 3/2015 | Maki et al. | |
| D806,256 S | 12/2017 | Allen et al. | |
| 10,201,457 B2 | 2/2019 | Maharaj et al. | |
| D858,778 S | 9/2019 | Foley et al. | |
| D876,647 S | 2/2020 | Lin | |
| D946,765 S | 3/2022 | Chen et al. | |
| D957,671 S | 7/2022 | Kiviat | |
| D964,572 S | 9/2022 | Kase | |
| D983,380 S | 4/2023 | Lear et al. | |
| D991,463 S | 7/2023 | Sepulveda | |
| D1,008,661 S | 12/2023 | Lehtonen | |
| 11,844,675 B1 | 12/2023 | Hoeprich et al. | |
| D1,028,254 S | 5/2024 | Li | |
| D1,028,255 S | 5/2024 | Zhang | |
| 2001/0022063 A1* | 9/2001 | Korteweg | A61F 15/001 53/435 |
| 2003/0130576 A1* | 7/2003 | Seeley | A61B 90/36 600/426 |
| 2007/0010844 A1* | 1/2007 | Gong | A61M 25/0108 606/192 |
| 2008/0015484 A1 | 1/2008 | Wolfensberger | |
| 2008/0177240 A1* | 7/2008 | Kemnitzer, II | A61F 15/001 206/570 |
| 2009/0099082 A1* | 4/2009 | Schoenberger | A61L 15/425 521/70 |
| 2009/0264990 A1* | 10/2009 | Bruszewski | A61F 2/07 623/1.13 |
| 2013/0035655 A1 | 2/2013 | Nakamura | |
| 2013/0079590 A1 | 3/2013 | Bengtson | |
| 2014/0171739 A1* | 6/2014 | Nguyen | A61B 1/3132 600/114 |
| 2014/0295134 A1 | 10/2014 | Wood et al. | |
| 2015/0182657 A1 | 7/2015 | Rieske et al. | |
| 2018/0344429 A1 | 12/2018 | Stewart | |
| 2019/0117464 A1 | 4/2019 | Seo et al. | |
| 2020/0390848 A1 | 12/2020 | Nair | |
| 2021/0338490 A1* | 11/2021 | Kieswetter | A61M 1/915 |
| 2022/0403590 A1 | 12/2022 | Yamashita | |

FOREIGN PATENT DOCUMENTS

| | | | | |
|---|---|---|---|---|
| GB | 1195623 A | | 6/1970 | |
| JP | 2013538629 A | * | 10/2013 | |
| WO | WO-2011014907 A1 | * | 2/2011 | A61F 13/36 |
| WO | WO-2012129270 A1 | * | 9/2012 | A61B 1/32 |
| WO | WO-2019042790 A1 | * | 3/2019 | A61B 5/1109 |

OTHER PUBLICATIONS

Creative Materials, 125-09TS Radio Opaque Ink, Nov. 29, 2017. (Year: 2017).*

International Search report and Written Opinion issued in International Application No. PCT/US2020/054293, mailed on Feb. 12, 2021, 13 pages.

International Preliminary Report issued in International Application No. PCT/US2020/054293, mailed on Apr. 5, 2022, 9 pages.

Extended European Search Report issued in European Application No. 20872988.9, mailed on Oct. 6, 2023, 10 pages.

Amazon, "80-20 Inc 3 Hole Straight Flat Plate," Apr. 11, 2014, [Retrieved on Jun. 25, 2024], 2 Pages, Retrieved from the Internet URL: https://www.amazon.com/80-20-30-4306-3-Hole-Joining/dp/B00JMEMOE4.

Amazon, "80-20 Inc 4 Hole Straight Flat Plate," Jan. 16, 2018, [Retrieved on Jun. 25, 2024], 2 Pages, Retrieved from the Internet URL: https://www.amazon.com/dp/B0792BFSHR.

Amazon, "Allaquix High Performance Stop Bleeding Gauze," Jan. 4, 2017, [Retrieved on Jun. 25, 2024], 4 Pages, Retrieved from the Internet URL: https://www.amazon.com/AllaQuix-Bleeding-Professional-Grade-First-Aid-Hemostatic/dp/B01N5M58EP.

Amazon, "Impresa White Liposuction Foam Pads," Apr. 10, 2019, [Retrieved on Jun. 25, 2024], 3 Pages, Retrieved from the Internet URL: https://www.amazon.com/Pack-Lipo-Foam-Liposuction-Compression/dp/B07QH7X659.

Medicalmonks, "Surgifoam Absorbable Gelatin Sponge," Sep. 8, 2021, [Retrieved on Jun. 25, 2024], 2 Pages, Retrieved from the Internet URL: https://medicalmonks.com/product/surgifoam-absorbable-gelatin-sponge/.

NHS, "Mallet Finger," esht.nhs.uk, Sep. 8, 2023, [Retrieved on Jun. 25, 2024], 4 Pages, Retrieved from the Internet URL: https://www.esht.nhs.uk/wp-content/uploads/2017/06/0167.pdf.

Ormanagement, "Alloderm Regenerative Tissue Matrix," [Retrieved on Jun. 25, 2024], 1 Page, Retrieved from the Internet URL: https://www.ormanagement.net/BuyersGuide/ProductView?id=1592.

Sntervention, "Swicker Radiopaque Surgical Foam Brochure," 2023, [Retrieved on Jun. 25, 2024], 2 Pages, Retrieved from the Internet URL: https://syntervention.com/wp-content/uploads/2024/01/LB3051-REV-01-SWICKER-brochure-12_23.pdf.

Syntervention, "Swicker Radiopaque Surgical Foam Sponge," May 16, 2022, [Retrieved on Jun. 25, 2024], 6 pages, Retrieved from the Internet URL: https://syntervention.com/swicker/ (Year: 2022).

Syntervention, "Swicker Surgical Sponge Overview," Youtube, Sep. 8, 2023, 2 Pages, Retrieved from the Internet URL: https://www.youtube.com/watch?v=dj8QXOOKUel.

Syntervention "Swiper Instructions for Use," Youtube, Feb. 6, 2014, 2 Pages, Retrieved from the Internet URL: https://www.youtube.com/watch?v=Q5gnnifYoeU.

WFLA, "New Surgical Foam Technology Offers Significant Benefits to Hospitals As Alternative to Conventional Surgical Products," Jun. 5, 2024, [Retrieved on Jun. 25, 2024], 4 Pages, Retrieved from the Internet URL: https://www.wfla.com/business/press-releases/ein-presswire/717321479/new-surgical-foam-technology-offers-significant-benefits-to-hospitals-as-alternative-to-conventional-surgical-products/.

* cited by examiner

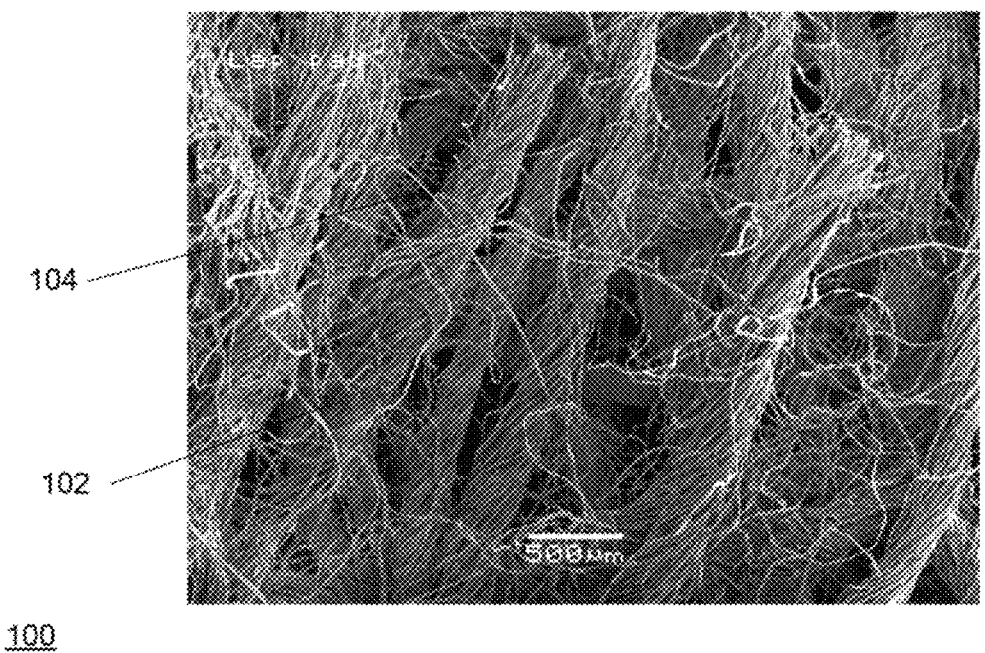
FIG. 1 – RELATED ART
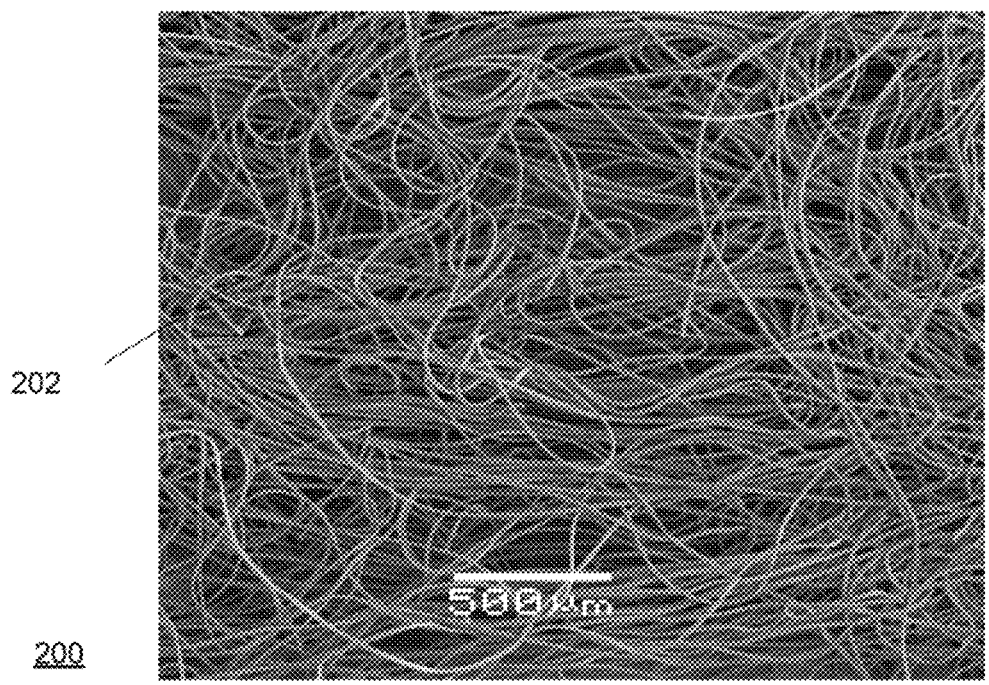
FIG. 2 – RELATED ART

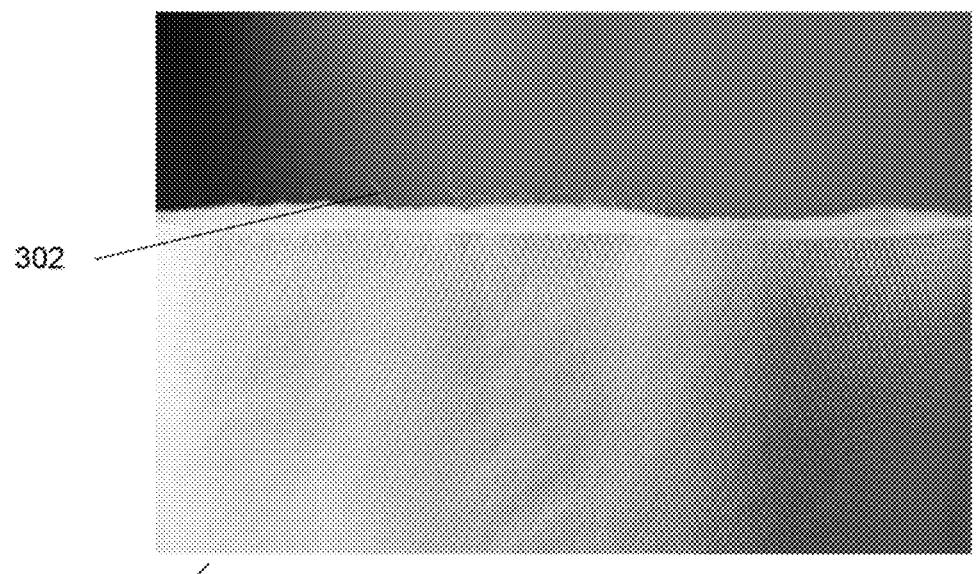
FIG. 3 – RELATED ART
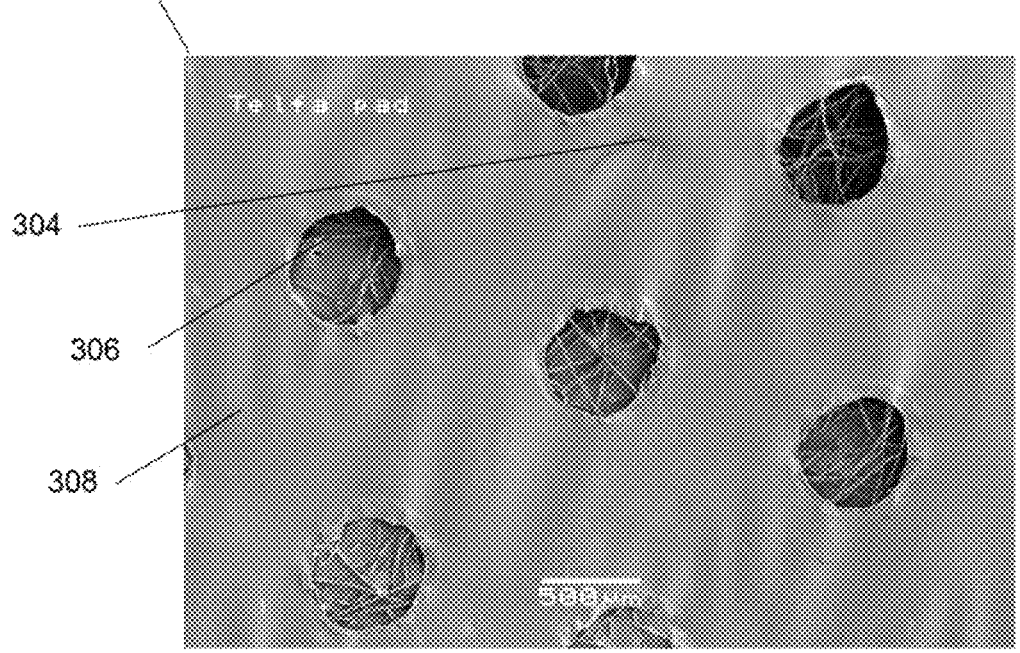
FIG. 4 – RELATED ART

MEDICAL DEVICE, METHOD OF USING AND MAKING THE SAME

CROSS-REFERENCE TO RELATED APPLICATIONS

The present application claims the benefit of and priority, under 35 U.S.C. § 119(e), to U.S. Provisional Patent Application No. 62/909,895 filed Oct. 3, 2019, which is incorporated herein by reference in its entirety.

BACKGROUND OF THE INVENTION

Field of the Invention

The present invention generally relates to medical devices, systems and methods for performing surgical procedures, and more particularly to reusable, biocompatible, cellulose-free medical hydrophilic or hydrophobic devices, systems, and methods for cleaning the absorption of blood and body fluids, temporary packings, hydration of tissues, tissue protection, organ transportation, dressings and the like in an operative site used during medical and surgical procedures.

SUMMARY OF THE INVENTION

Accordingly, the invention is directed to a medical device, method of using and making the same that substantially obviates one or more of the problems due to limitations and disadvantages of the related art.

An advantage of the invention is to provide a system that allows for a reduction of medical waste, e.g., reducing the number of medical sponges or medical gauze used in a procedure.

Yet another advantage of the invention is to provide a reusable sponge or wipe in the same procedure.

Another advantage of the invention is to provide a medical device that is cellulose- and lint-free with ultra-low particle count.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, one embodiment is directed towards a sterile pre-hydrated packaged medical device for use during medical procedures. The pre-hydrated packaged medical device includes a sterile pre-hydrated hydrophobic foam material having a length, width, and height. The open celled foam is saturated with a sterile saline fluid and has an ultra-low particle count. The pre-hydrated hydrophobic foam material includes about 20 grams of sterile saline fluid in the package.

In another aspect of the present invention, one embodiment is directed towards a disposable open celled foam medical device for use during medical procedures. The disposable medical device has hydrophobic open celled foam material including a plurality of holes or cells. The holes or cells travel through an entire dimension of the hydrophobic open celled foam material. The foam material includes an ultra-low particle count and has a bacterial endotoxin level under 20.0 EU/medical device.

In still another aspect of the present invention, one embodiment is directed towards a method of performing a medical procedure. The medical procedure includes providing a pre-hydrated hydrophobic medical device arranged in a closed package. The medical device includes a sterile pre-hydrated hydrophobic open celled foam material having a length, width, and height. The foam material is saturated with a saline solution had has an ultra-low particle count. The method further includes removing the pre-hydrated medical device from the closed package and removing some of the sterile saline fluid by manually wringing the medical device. The method further includes using the medical device in the operating field to remove a material or substantially remove a material from a secondary device and discarding the medical device.

In yet another aspect of the present invention, one embodiment is directed towards a method for performing a medical procedure with a reusable multi-use surgical medical device by providing the reusable multi-use surgical medical device including an open-celled reticulated foam material having an ultra-low number of particles and a plurality of radiopaque (RO) ink markers adhered to a surface of the reticulated foam material configured to be visible under an imaging device at various orientations. The medical device has a bacterial endotoxin level below at least 20.0 EU/medical device. The method further includes initially applying a solution to the reusable multi-use surgical medical device to condition for use and removing the reusable multi-use surgical medical device from the solution and releasing residual solution by manual wringing. The method further includes manipulating the conditioned reusable multi-use surgical medical device through a lumen of a trocar to clean the lumen of the trocar or condition the trocar. During this method, the conditioned multi-use surgical medical device does not fragment. Optionally, the reusable multi-use surgical medical device can be used again to clean other devices during the procedure, e.g., camera and other instruments.

In still another aspect of the present invention, one embodiment is directed towards a medical device for use during medical procedures including a laundered hydrophilic foam material having a length, width, height, and thickness, wherein the foam material is an open celled reticulated foam. The foam has an ultra-low particle count and optionally is pre-hydrated hydrophobic foam with a solution. The foam also optionally includes one or more imaging markers, e.g., radiopaque (RO) ink, radiopaque (RO) tag or string adhered to the foam, and radio frequency identification (RFID) tag. Optionally and/or alternatively, the medical device can be packaged in a non-hydrated or in a dry state. Optionally and/or alternatively, the medical device does not have to be sterile or sterilized for some non-medical applications.

In yet another aspect of the present invention, one embodiment is directed towards a reusable multi-use surgical medical device for use during a medical procedure. The device includes a laundered hydrophilic foam material having an ultra-low number of particles configured to absorb bodily fluids. The device can be rinsed and reused repetitively during the same procedure. The device also optionally includes a plurality of radiopaque (RO) ink markers adhered to a surface of the foam material configured to be visible under an imaging device at various orientations. The device has a bacterial endotoxin level below at least 20.0 EU/medical device.

In still another aspect of the present invention, one embodiment is directed towards a reusable multi-use surgical medical device for use during a medical procedure. The medical device includes a laundered hydrophobic foam material having an ultra-low number of particles configured to be rinsed and reused repetitively during the medical procedure. The device also optionally includes a plurality of radiopaque (RO) ink markers adhered to a surface of the foam material configured to be visible under an imaging device at various orientations. The device has a bacterial endotoxin level below at least 20.0 EU/medical device.

In another aspect of the present invention, one embodiment is directed towards a method for performing a medical procedure with a reusable multi-use surgical medical device including providing the reusable multi-use surgical medical device comprising an open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition for use and removing the reusable multi-use surgical medical device from the solution and releasing residual solution by manual wringing. The method further includes manipulating the conditioned reusable multi-use surgical medical device in an operating field to absorb blood, body fluids, water and other aqueous liquids in an operative site of the operating field. The method further includes returning the now-used reusable multi-use surgical medical device to the solution to clean and rinse it and repeating these steps, as necessary.

In yet another aspect of the present invention, one embodiment is directed towards a method for performing a medical procedure with a reusable multi-use surgical medical device including providing the reusable multi-use surgical medical device comprising an open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition for use and removing the reusable multi-use surgical medical device from the solution and releasing residual solution by manual wringing. The method further includes hydrating a tissue or organ of a patient by arranging the conditioned reusable multi-use surgical medical device adjacent to the organ or tissue during the medical procedure.

In still another aspect of the present invention, one embodiment is directed towards a method for performing a medical procedure with a reusable multi-use surgical medical device including providing the reusable multi-use surgical medical device comprising an hydrophilic open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition for use. The method further includes removing the reusable multi-use surgical medical device from the solution and releasing residual solution by manual wringing. The method further includes arranging the reusable multi-use surgical medical device under a medical instrument to protect and hydrate tissue or organ of a patient by during the procedure.

In yet another aspect of the present invention, one embodiment is directed towards a medical kit including one or more medical devices as described with reference to any embodiment herein and instructions for use.

This Summary section is neither intended to be, nor should be, construed as being representative of the full extent and scope of the present disclosure. Additional benefits, features and embodiments of the present disclosure are set forth in the attached figures and in the description hereinbelow, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 illustrates a magnified view of a cellulose laparotomy pad for the absorption of discharges according to the related art.

FIG. 2 illustrates a magnified view of a cellulose gauze for use with medical procedures according to the related art.

FIG. 3 illustrates a non-magnified view of a non-adherent pad according to the related art.

FIG. 4 illustrates a magnified view of a non-adherent pad according to the related art.

DETAILED DESCRIPTION OF THE ILLUSTRATED EMBODIMENTS

Figure 5:
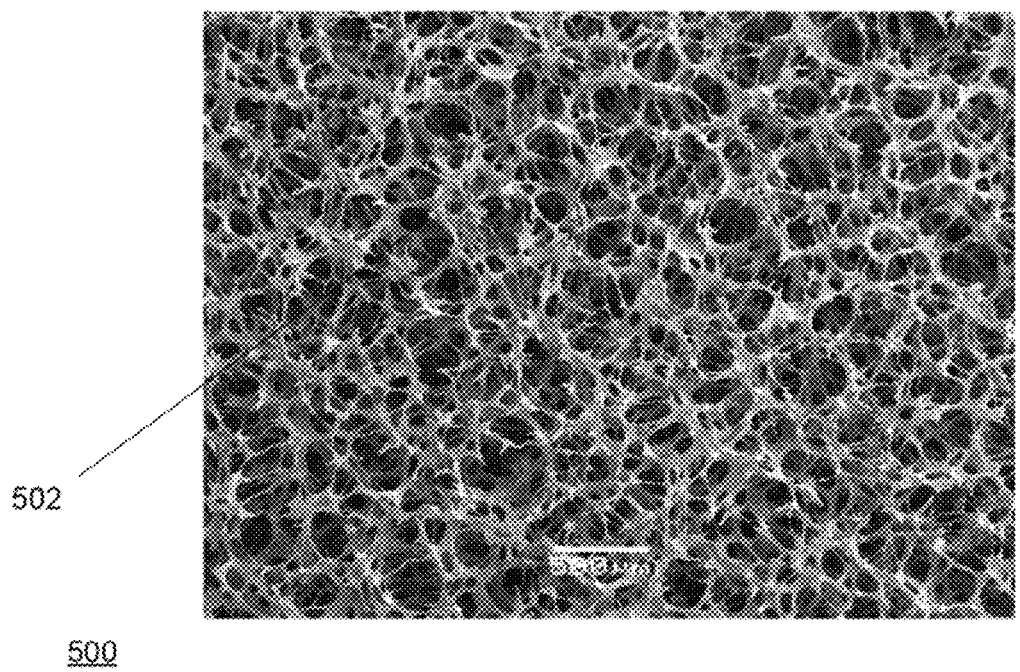
FIG. 5 illustrates a magnified view of a medical device according to an implementation of the present disclosure.

Persons skilled in the art will readily appreciate that various aspects of the present disclosure can be realized by any number of methods and articles configured to perform the intended functions. Stated differently, other methods and articles can be incorporated herein to perform the intended functions. It should also be noted that the accompanying figures referred to herein are not all drawn to scale, but may be exaggerated to illustrate various aspects of the present disclosure, and in that regard, the figures should not be construed as limiting. Finally, although the present disclosure may be described in connection with various principles and beliefs, the present disclosure should not be bound by theory. The following detailed description describes a medical device, method of using and making, and is presented to enable any person skilled in the art to make and use the disclosed subject matter in the context of one or more particular implementations. Various modifications, alterations, and permutations of the disclosed implementations can be made and will be readily apparent to those skilled in the art, and the general principles defined may be applied to other implementations and applications, without departing from scope of the disclosure. The present disclosure is not intended to be limited to the described or illustrated implementations, but to be accorded the widest scope consistent with the described principles and features.

In order to more fully appreciate the present disclosure and to provide additional related features, the following references are incorporated therein by reference in their entirety:

(1) U.S. Pat. No. 3,566,871 by Richter, which discloses a hydrophilic polyurethane sponge adapted for medical usage, in which the sponge pores contain a surfactant coating to accelerate absorption of body fluids into the pores at medically preferred rates, the fluids being retained therein by capillarity to affect removal of the fluids from the body. The sponge is flexible and substantially free from lint, toxicity, and abrasiveness, making it particularly suitable for use as a surgical laparotomy pad.

(2) U.S. Pat. No. 7,291,762 by Flick, disclosing a dressing for promoting healing and pain relief of the body of a living organism having a pathologic condition has at least one layer of conductive material having a resistance no greater than 1000 Q/cm2. When placed proximate to a portion of the body of the living organism suffering from the pathologic condition, the dressing alters the electrodynamic processes occurring in conjunction with said pathologic condition to promote healing and pain relief in the living organism. When used as a wound dressing, the conductive material is placed in contact with tissue around the periphery of the wound and with the wound, lowering the electrical potential and resistance of the wound and increasing the wound current. In an exemplary embodiment, the conductive material is a multi-ply nylon fabric plated with silver by an autocatalytic electroless plating process and with the plies in electrical continuity. The dressing provides an antimicrobial and analgesic effect. The dressing may be provided for numerous applications and may include other layers such as an absorbent layer, a semi-permeable layer and additional layer of conductor material. Multilaminate embodiments of the present invention exhibit conductive material concentration gradients and, potentially, a capacitive effect when sequential conductor layers are insulated by intervening layers.

(3) U.S. Patent Application Publication No. 2013-0079590, by Bengston, which discloses novel surgical sponge-pad devices that are highly absorbent, durable, and reusable. The technical features of the surgical sponge-pad devices make possible unique surgical sponge-pad systems and methods that take advantage of the use, conditioning, and reuse of a single surgical sponge device again and again during a surgical procedure. The invention provides surgical-sponge-pad devices, systems, and methods that make possible a significant reduction in the number of surgical sponges needed for a given surgical procedure. In addition, this multifunctional surgical sponge-pad will have significant and brand new applications in surgery for the protection and hydration of tissues, transmission of antibiotics and antimicrobials and other solutions, barriers in surgery and even use in transfer of transplanted organs as well as many other future medical and surgical uses as yet undefined and undiscovered.

An embodiment of the invention is a medical device configured as a hydrophobic or hydrophilic sponge with an open-cells with imaging features configured to be visible under x-ray, ultrasound wands or other imaging devices. The medical device is durable, moldable, lint free, cellulose free, ultra-low particles, washable and reusable within the same surgical case, non-toxic based on cytotoxicity reports, and has bacterial endotoxin levels below about 20.00 EU/device. The standard for finished medical devices is a bacterial endotoxin limit not of more than 20.0 EU/device. In addition, the bacterial endotoxin limit for medical devices in contact with cerebrospinal fluid is not more than 2.15 EU/device and the endotoxin limit for medical devices in contact with intraocular ophthalmic devices is not more than 0.2 EU/device. In one embodiment, the medical bacterial endotoxin limit is below 10.0 EU/device, in a preferred embodiment the limit is below 7.00 EU/device and in a more preferred embodiment the limit is below 1 EU/device.

The medical device can be used to clean other medical devices, instruments or used in the manufacturing of other medical devices to avoid particulate contamination.

In one implementation, the device is configured in a pre-hydrated package such that the foam material is saturated or partially saturated with a fluid, e.g., sterile saline, pharmacological agent, and the like. The pharmacological agent can include one or more of antibiotic, saline, heparin sodium, anti-thrombotic, thrombotic agent, analgesic, anti-inflammatory, anesthetic, and others or combinations of the same. In one implementation, the pre-hydrated package includes at least 20 grams of fluid or more.

In one implementation, the medical device is configured to prevent contamination, e.g., fiber contamination, particulate or particle contamination and other contamination, and related complications and risks during medical procedures, e.g., invasive procedures.

In one implementation, the medical device is configured to resist abrasion and falling apart during use.

In one implementation, the medical device includes either a hydrophilic or hydrophobic foam material that is laundered to reduce contaminants and particulates and particles. The laundering is done with low particulate water (LPW) that is filtered with a twin 0.1 micron filter system and repeated for a predetermined number of times.

In one implementation, the medical device includes a foam material configured to be used in a medical procedure, e.g., for the removal of blood, contrast and other contaminants from sterile instruments and medical devices.

In one embodiment, the medical device includes a foam material constructed from one or more of a polyurethane material, polyester material, and combinations of the same. The foam material is reticulated foam in one embodiment.

In one implementation, the foam material may have one or more of the following physical properties determined by ASTM Standards as known in the art, e.g., ASTM D3574. The properties include one or more of a pore size in a range from about 50 to about 200 ppi, with a pore size of 75-99 ppi in a preferred embodiment; a density in range from about 1.5 lb/ft$^3$ to about 2.5 lb/ft$^3$, with a density of about 1.8 lb/ft$^3$ to about 2.2 lb/ft$^3$ in a preferred embodiment; a tensile strength in a range from about 20 psi to about 40 psi, with a tensile strength of 30 psi in a preferred embodiment; an elongation in range from about 300 to 500 percent, with an elongation of about 380 percent in a preferred embodiment; and a compression set at 50% of about 10 percent to about 30 percent, with a compression set of about 20 percent in a preferred embodiment.

In another embodiment, the foam material was polyurethane reticulated foam with open celled pores having one or more of the following physical properties determined by ASTM Standards as known in the art, e.g., ASTM D3574: a pore size of about 75 to about 85 ppi, density of about 1.8 to about 2.2 lb/ft$^3$, tensile strength of 30 psi, elongation of 380 percent, tear strength 3.6 lbs/in, CLD @ 25% R of about 0.2 psi, CLD @ 65% R of about 0.4 psi, and compression set @ 50% of about 20 percent max.

In one implementation, the medical device includes a foam material such as an open celled foam material made up of cells that are open, a closed cell foam material made up of cells that are closed, and a combination of closed cell foam material and open cell foam material. The combination of an open cell foam material and closed cell foam material may be continuous or discontinuous, e.g., a first portion is 100 percent open cell foam and a second portion is 100 percent closed cell foam. In one implementation, the foam material may be homogenous of open and closed cell foam.

In one embodiment, the foam material of the medical device is open-cell foam polyurethane reticulated foam.

In one embodiment, the foam material of the medical device does not include holes all the way through the material. Rather, in this embodiment, the foam material includes multiple holes having a dimension of 0.03 inches or less. These multiple holes do not go all the way through a length dimension, a width dimension, or a height dimension of the foam material.

In one embodiment, the medical device is extremely pliable, soft, and non-abrasive after rehydration with a solution, e.g., saline, and other solutions described herein.

In one embodiment, the foam material described herein has the ability of a material to absorb energy when it is deformed elastically, and release that energy upon unloading. That is, the material is also configured in a predetermined shape and will return to its predetermined shape after the application of force has been removed. That is, the material can be deformed with force, but will return to its condition after the removal of force.

In one embodiment, the medical device includes a foam material that does not include one or more of a latex material, does not include bisphenol A (BPA), does not include di(2-ethylhexyl) phthalate (DEHP), and does not include cellulose. Accordingly, the medical device is a biocompatible material and it is believed the use of the medical device described herein with the foam material will reduce surgical site infections (SSI) and/or reduce hospital acquired infections (HAI) as compared to traditional sponges and/or gauze materials.

In one embodiment, the medical device includes a foam material that is a hydrophilic material, e.g., the foam material is formed with highly absorbent material, e.g., absorbent foam. Highly absorbent foam means a versatile hydrophilic foam that will absorb up to five times or more of its weight in fluids. In one implementation, highly absorbent foam means a versatile hydrophilic foam that will absorb up to ten times or more of its weight in fluids. In one implementation, highly absorbent foam means a versatile hydrophilic foam that will absorb up to 15 times or more of its weight in fluids. Hydrophilic means the property of attracting or associating with water molecules, possessed by polar radicals or ions, as opposed to hydrophobic.

In one embodiment, the medical device with the hydrophilic foam material can absorb up to twenty times its weigh in saline solution. The medical device is configured for the removal of blood, contrast, and other contaminants from medical devices such as sterile instruments, guidewires, and other devices. The medical devices are easy to handle and are bendable, conformable, durable and non-shredding.

In one embodiment, the hydrophilic material is a flexible polyurethane foam that has the following physical characteristics: a melting point in a range from about 350 to about 375 F, density in a range from about 1.1 lbs/cfc to about 20 lbs/cfc, and insoluble in water.

In one embodiment, the foam material is a hydrophobic material. Hydrophobic means configured to repel water, insoluble in water and not readily capable of absorbing water.

In one embodiment, the edge includes one or more of a chamfered edge or a beveled edge. A chamfered edge is a transitional edge between two adjoining right-angled faces of the foam material. A beveled edge is an edge that are not perpendicular to one another of the foam material. A chamfer edge is technically a type of bevel edge, but the difference between the two is that a bevel is an edge that is sloped and a chamfer is an edge that connects two surfaces at a 45-degree angle, while a bevel's slope can be any angle except 90 or 45 degrees.

As used herein particulate is a manufacturing particulate or particle and is something that occurs in the manufacturing process and is not a cellulose, e.g., plant-based, particulate.

Table 1 shows the number of particles associated with medical devices described with reference to embodiments and related art devices. Each of the medical devices were tested for particles as described herein.

TABLE 1

Particulate Summary

| Foam Material Type* | Size [inches] | No. of particles ≥5 μm [particles/cm²] | No. of particles ≥10 μm [particles/cm²] | No. of particles ≥25 μm [particles/cm²] | No. of particles ≥50 μm [particles/cm²] | No. of particles ≥100 μm [particles/cm²] | Test Method |
|---|---|---|---|---|---|---|---|
| Hydrophilic | 3 × 3 × 0.5 | n/a | 5,791 | 41 | 0 | 0 | LO |
| Hydrophilic | 3 × 3 × 0.5 | 276 | n/a | n/a | n/a | n/a | LPC |
| Hydrophilic | 9 × 9 × 0.5 | n/a | 81,740 | 2,549 | 0 | 0 | LO |
| Hydrophilic | 9 × 9 × 0.5 | 9,259 | n/a | n/a | n/a | n/a | LPC |
| Lap Pad | 15 × 15 | n/a | 84,330 | 6,070 | 530 | 200 | LO |
| Raytec sponges | 4 × 4 | n/a | 56,210 | 1,426 | 24 | 0 | LO |
| Lap Pad | 15 × 15 | 23,373 | 0 | 0 | 0 | 0 | LPC |
| Raytec sponges | 4 × 4 | 18,850 | 0 | 0 | 0 | 0 | LPC |
| Hydrophobic | 3 × 3 × 0.25 | n/a | 2,090 | 60 | 2 | 0 | LO |
| Cotton Gauze | 4 × 4 | n/a | 29,809 | 937 | 8 | 0 | LO |
| Telfa (non-adherent pads) | n/a | n/a | 27,884 | 2,401 | 111 | 0 | LO |

*Each of the foam materials was laundered in an aqueous solution to remove manufacturing particulates. The number of particles were measured with a Light Obscuration (LO) system and techniques as known in the art or a Liquid Particle Counting (LPC) system and techniques as known in the art.

Referring to Table 1, the related art medical devices made from cellulose including gauze, Telfa non-adherent pads, Lap Pad and Raytec each have a much higher number of particles at various sizes compared to the embodiments of medical devices described herein. Moreover, it is believed the higher the number of particles is evidence of contamination and potential related medical complications and risks to patients during invasive medical procedures. For example, the high number of particles can also be indicative of fibers or other contaminates.

The related art devices of cotton gauze and Telfa pads contain cellulose and fibers. It has been found that fibers associated with the related art medical devices, e.g., cotton gauze and Telfa pads, can stick to guide wires, sheaths, catheters, or other medical components/devices used in a medical procedure. Also, the fibers, particles or other contaminates may be found in syringes and saline bowls used during medical procedures. For example, if cotton gauze or Telfa pads are used to clean a guidewire or stent the fibers can be transferred to the stent or guidewire and end up in the patient. The fibers of the cotton gauze or Telfa pads can also snowplow or pile up in location of a guidewire or other medical device making the guidewire difficult to use or potentially unusable. In addition, it is believed one or more of these complications can occur in patients with related art device cotton gauze if fiber is transferred to the patient: inflammation, granuloma, occlusive granuloma, thrombus formation, e.g., myocardial infarction and stroke, adhesions, restenosis, infection, necrosis, kidney problems or failure, allergic reactions, and misdiagnosed carcinomas.

It is believed that transmission of the fibers, particles, or other contaminates to the patient by related art devices, e.g., cotton gauze or Telfa pads, can occur by cleaning or wiping medical devices. Also, soaking the related art devices, e.g., cotton gauze or Telfa pads, in procedure bowls and drawing up the flush into a syringe and injecting it into catheters or sheaths to clear or to flush the catheter lumen may transfer the containments to the patient. Moreover, handling the related art devices, e.g., cotton gauze or Telfa pads, with sterile gloves may result in subsequent transfer of fibers from the gloves to the medical devices used in the procedure.

The high number of particles or fibers in the related art are also believed to be a factor in surgical site infections (SSI) or hospital acquired infections (HAI). For example, it is believed the cellulose is not digested by tissue, macrophages, or other cells. A cascade of inflammatory reactions can occur from the contaminants, e.g., cellulose, particles, or other, forming foreign body granulomas and contribute to post-operative complications, e.g., adhesions, SSI, and HAI. Unintentional foreign body emboli remain common in modern angiographic practice and are underappreciated clinically and particulate embolization, e.g., fiber, is present in as many as 25% resected arteriovenous malformations. Shannon, et al., Inadvertent Foreign Body Embolization in Diagnostic and Therapeutic Cerebral Angiography, AM J. Neuroradiology, February 2006, 27, 278-282. Moreover, a stent study found that forty-two percent of patients with stent thrombosis had particulates (glove powder and lint fibers) enmeshed with the thrombi. Whelan, et al., Foreign Body Contamination During Stent Implantation Catherization and Cardiovascular Diagnosis, March 1997; 40 (3), 328-332. Gauze fibers have been found adhered to a guide wire between the tip of a balloon catheter and the y-adapter. Gauze fibers have been found lodged on a stent strut from handling with sterile gloves. Particulate entry points to the patient include at least blood vessels, open wounds, closed wounds via sheath, inhalation, and a medical device during handling. Some particulate transmission methods to a patient include wiping various medical devices or instruments with sponges or gauzes, contacting the patient with those sponges or gauzes or instruments and medical devices that have been in contact with those sponges or gauzes, fluid injection, airborne particulates and with surgical gloves that have come in contact with the sponges or gauzes.

Also, embolization of cotton fibers during coronary and neuro interventional procedures has been shown to cause arterial thrombosis potentially leading to myocardial infarction and/or stroke.

The medical devices having foam material as described in embodiments and Table 1 do not contain cellulose and have reduced or ultra-low particles, thereby these medical devices are believed to reduce post-operative complications, SSI, HAI. These complications increase medical costs significantly and overall health care costs.

In addition, the medical devices having foam material as described in embodiments and Table 1 are re-usable during a medical procedure. In one embodiment, the medical device may be reused by washing in a surgical bowl with saline or other solution described herein. In contrast, the cotton gauze or other related art devices are not reusable, thereby increasing the amount of medical waste. Medical waste is costly to dispose and thereby the related art devices are more expensive to use as there is more medical waste. Also, the related art devices, e.g., cotton gauze and Telfa pads, are not reusable, thereby also increasing the total number of particles or fibers per procedure as more than one is typically used, e.g., 1 medical device reused vs. 35 of the related art devices.

In one embodiment, the medical device with foam material is reusable and either hydrophilic or hydrophobic and has no cellulose, low or ultra-low particle levels, no latex, no bisphenol A (BPA), no di(2-ethylhexyl) phthalate (DEHP), bacterial endotoxin less than 20.00 EU/device, and is non-cytotoxic. In one embodiment, the medical device is lint free and cellulose free. In one embodiment, the medical device has no cytotoxins. In one embodiment, the medical device has bacterial endotoxins below about 20.0 EU/medical device, and in a preferred embodiment below about 10.0 EU/medical device and in a more preferred embodiment below about 7.0 EU/medical device. In one embodiment, the medical device is non-abrasive and configured to not disintegrate with use.

In one embodiment, the foam material can be configured into any two-dimensional or three dimensional geometric dimension, e.g., round shape, ball shape, triangle shape, square shape, rectangle shape, oval shape, diamond, and combinations of the same and the like.

In one embodiment, the foam material can be configured into any preformed dimension or design such as a curved shape, block shape, circle shape, trench shape, triangle shape and combinations of the same and the like.

In one embodiment, the foam material is configured as a glove or mitten to allow it to be worn by a user in any conventional size, e.g., small, medium, large, and extra-large. The glove may include slots for one or more fingers, e.g., one finger, two fingers, three fingers, etc., or be a mitten. In one implementation, the glove or mitten can be used to clean out a wound, e.g., absorb blood or other fluids. Optionally or alternatively, the foam material is configured into a shape that covers or partially covers one finger, e.g., a finger sock or two fingers.

In one implementation, the foam material may include any type of pattern or texture on a surface of the foam material, e.g., cross-hatched pattern, three-dimensional pattern, wave pattern, linear pattern, non-linear pattern, and combinations of the same. The texture or pattern can be formed with a laser, heat, or during the manufacturing process.

In one implementation, the foam material can be configured into one of a 1 inch by 1 inch dimension, 1 inch by 3 inch dimension, a 6 inch by 3 inch dimension, or a twelve inch by 12 inch dimension with a thickness in a range from about 0.1 inch to 1 inch or greater. The thickness can vary throughout the dimension.

In one embodiment, the medical device may have the one of the following dimensions, 0.5×3×0.25 inches, 1×3×0.25 inches, 3×3×0.25 inches, 3×9×0.25 inches, 6×9×0.25 inches, 9×9×0.25 inches, 0.5×3×0.5 inches, 1×3×0.5 inches, 3×3×0.5 inches, 3×9×0.5 inches, 6×9×0.5 inches, and 9×9×0.5 inches.

In another embodiment, the medical device can have a thickness dimension in a range from about 0.1 inch to about 1 inch or greater, a length dimension in range from about 0.5 inch to about 12 inches or greater and a width dimension in range from about 0.5 inch to about 12 inches or greater.

In one embodiment, the foam material is configured into any color or any combination of colors, e.g., any combination of red, yellow, and blue colors. In one implementation, the foam material includes one or more of a yellow color, an orange color, a pink color, a white color, and a fluorescent color.

In one implementation, the foam material is configured with one or more of a logo, brand, or combination, e.g., laser etched brands/logos, laser etched designs and combinations of the same.

In one implementation, the device can be preformed into sheets with perforations in a predetermined dimension to permit separation into individual units.

In one implementation, the device including the foam material can be cut into any desired shape.

In one implementation, the device including the foam material is foldable or malleable into various shapes and sizes during a procedure.

In one implementation, the medical device includes a foam material and includes a backing material to provide more rigidity to the medical device. The backing material can include a plastic material, a thermoplastic material, a paper material, a cardboard material, a cloth material, and combinations of the same, to give the medical device more rigidity.

In one implementation, the medical device includes a foam material that includes a graphic or pattern on a surface of the medical device. The graphic or pattern can be applied to the surface by any known means in that art, e.g., printed, adhered to a surface, stained on a surface, or combinations of the same. In one embodiment, the graphic may include dimensions, lines, grids, labels, or other measurement indica.

In one implementation, the medical device has a foam material that is coated with a pharmacological agent that can include one more of antibiotic, saline, heparin sodium, anti-thrombotic, thrombotic agent, analgesic, anti-inflammatory, anesthetic, and others or combinations of the same. In one implementation, the pre-hydrated package includes at least 20 grams of fluid or more.

As used herein a pyrogen is a substance, typically produced by a bacterium, which produces fever when introduced or released into the blood. As used herein particulates and particles of the same typically result from the manufacturing process.

In one implementation, the foam material can include imaging markers, e.g., radiopaque (RO) material configured as a RO marker, echogenic material configured as an echogenic marker, and combinations of the same. The imaging markers are configured to be detectable or visible under ultrasound or other visualization instrument, x-ray imaging or other imaging device. The imaging markers are configured to prevent leaving the medical device in the patient after the procedure. For example, in order to ensure no medical devices are left in the body a user can image the patient with an imaging device that will detect the one of the imaging markers. If no imaging markers are detected then the user can verify that no medical devices are left in the user.

The imaging markers may be attached to the foam material with an adhesive, embedded in the foam material, attached to the foam material with heat, sewn into the material or attached by other means as known in the art. The markers may be arranged in a pattern configured to assist with the orientation of the device, e.g., up, down, side, etc. The markers may be arranged in any corner or all corners of the device. The markers may be arranged in a grid configured at predetermined distance, so they can be used to determine distances.

Optionally and/or alternatively, the imaging material, e.g., RO material can be applied as an ink. The RO ink can be applied as a continuous shape, a discontinuous shape, or a combination of the same. The line may be as dots, dashed and combination of the same. The RO including can be applied in various patterns, e.g., grid patterns. The grid pattern appears to show up clearly in with x-ray imaging. It is believed that applying the dots and/or dashes rather than a solid line of RO ink provides a more aesthetic appearance as the foam material of the medical device expands.

The RO ink is a radiopaque (RO) ink or a coating that can be applied by screen printing, printing, dipping, or other dispensing. The RO ink has excellent adhesion to the medical device foam material and is resistant to abrasion, scratching, flexing, and creasing. In one embodiment, the RO ink has a viscosity in a range from about 1 to about 50,000 cps and to paste cps, percent filter is greater than 90 percent. In one embodiment, the ink may be any in configured to be visible under x-ray and other imaging technologies.

Optionally and/or alternatively, the imaging material can be applied to a fabric or string that can be sewn into the foam material.

Optionally and/or alternatively, the imaging marker can be a radio frequency identification device (RFID), e.g., a RFID tag. The RFID can be implanted, embedded and/or adhered to the medical device including the foam material. The RFID tag can be enclosed in the medical device. Optionally and/or alternatively, the RFID device is biocompatible and can be hermetically sealed in a cover or coating. Alternatively, the sealed container may be injected into the body of the foam material of the medical device. The RFID tag may store information about medical device including manufacturer, model number and serial number. The RFID tag may also store information about a treating physician and/or patient including the treating physician's name and contact information, the patient's name, contact information, medical condition, treatment, and other relevant information. The RFID tag is also detectable by an external detection device and is configured to prevent leaving the medical device in the patient after the procedure. For example, in order to ensure no medical devices are left in the body a user can use an external device, e.g., scanner or the like, to detect the RFID tag. If no RFID tags are detected then the user can verify that no medical devices are left in the patient.

In one implementation, the foam material can include a coating including one or more of an anti-friction coating, e.g., a polytetrafluoroethylene coating, an anti-bacterial coating, an anti-fungal coating, a hydrophilic coating, an electrically charged coating and combinations of the same.

In one implementation, the foam material does not contain a surfactant or any other coatings.

In one implementation, the foam material is constructed from a thermoplastic material, polyurethane material, polyester material, polytetrafluoroethylene material, poly(vinyl alcohol) material, and combinations of the same and the like.

In a preferred embodiment, the foam material is a blend of polyester and polyurethane materials.

In one embodiment, the medical device is individually packaged, e.g., packaged in a hemostatic pouch, thermoplastic pouch, a Tyvek pouch or the like and boxed up. The sterilized packaged medical device has a shelf life of up to five years and the non-sterilized packaged medical device has a shelf life of up to 10 years.

In one embodiment, the medical device is sterilized by one or more of gamma radiation and ethylene oxide. Optionally and/or alternatively, the medical device can be non-sterile and placed on a tray and then sterilized with one or more of gamma radiation and ethylene oxide.

One embodiment is directed towards a sterile pre-hydrated packaged medical device for use during medical procedures. The pre-hydrated packaged medical device includes a sterile pre-hydrated hydrophobic foam material having a length, width, and height. The open celled foam is saturated with a sterile saline fluid and has an ultra-low particle count. The pre-hydrated hydrophobic foam material includes about 20 grams of sterile saline fluid in the package.

One embodiment is directed towards a disposable open celled foam medical device for use during medical procedures. The disposable medical device has hydrophobic open celled foam material including a plurality of holes or cells. The holes or cells travel through an entire dimension of the hydrophobic open celled foam material. The foam material includes an ultra-low particulate count and has bacterial endotoxin levels of less than 20.0 EU/device.

One embodiment is directed towards a method of performing a medical procedure. The medical procedure includes providing a pre-hydrated hydrophobic medical device arranged in a closed package. The medical device includes a sterile pre-hydrated hydrophobic open celled foam material having a length, width, and height. The foam material is saturated with a saline solution had has an ultra-low particulate count. The method further includes removing the pre-hydrated medical device from the closed package and removing some of the sterile saline fluid by manually wringing the medical device. The method further includes using the medical device in the operating field to remove a material or substantially remove a material from a secondary device and discarding the medical device.

One embodiment is directed towards a method for performing a medical procedure with a reusable multi-use surgical medical device by providing the reusable multi-use surgical medical device including an open-celled reticulated foam material having an ultra-low number of particles and a plurality of radiopaque (RO) ink markers adhered to a surface of the reticulated foam material configured to be visible under an imaging device at various orientations. The medical device has a bacterial endotoxin level below at least 20.0 EU/medical device. The method further includes initially applying a solution to the reusable multi-use surgical medical device to condition for use and removing the reusable multi-use surgical medical device from the solution and releasing residual solution by manual wringing. The method further includes manipulating the conditioned reusable multi-use surgical medical device through a lumen of a trocar to clean the lumen of the trocar or condition the trocar. During this method, the conditioned multi-use surgical medical device does not fragment.

One embodiment is directed towards a medical device for use during medical procedures including a laundered hydrophilic foam material having a length, width, height, and thickness, wherein the foam material is an open celled reticulated foam. The foam has an ultra-low particulate count and optionally is pre-hydrated hydrophobic foam with a solution. The foam also optionally includes one or more imaging markers, e.g., radiopaque (RO) ink, radiopaque (RO) tag or string adhered to the foam, and radio frequency identification (RFID) tag.

One embodiment is directed towards a reusable multi-use surgical medical device for use during a medical procedure. The device includes a laundered hydrophilic foam material having an ultra-low number of particles configured to absorb bodily fluids. The device can be rinsed and reused repetitively during the same procedure. The device also optionally includes a plurality of radiopaque (RO) ink markers adhered to a surface of the foam material configured to be visible under an imaging device at various orientations. The device has a bacterial endotoxin level below at least 20.0 EU/medical device.

One embodiment is directed towards a reusable multi-use surgical medical device for use during a medical procedure. The medical device includes a laundered hydrophobic foam material having an ultra-low number of particles and is configured to be rinsed and reused repetitively during the medical procedure. The device also optionally includes a plurality of radiopaque (RO) ink markers adhered to a surface of the foam material configured to be visible under an imaging device at various orientations. The device has a bacterial endotoxin level below at least 20.0 EU/medical device.

One embodiment is directed towards a method for performing a medical procedure with a reusable multi-use surgical medical device including providing the reusable multi-use surgical medical device comprising an open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition it for use and removing the reusable multi-use surgical medical device from the solution and releasing residual solution by manual wringing. The method further includes manipulating the conditioned reusable multi-use surgical medical device in an operating field to absorb blood, body fluids, water and other aqueous liquids in an operative site of the operating field. The method further includes returning the now used reusable multi-use surgical medical device to the solution to clean and rinse it and repeating steps, as necessary.

One embodiment is directed towards a method for performing a medical procedure with a reusable multi-use surgical medical device including providing the reusable multi-use surgical medical device comprising an open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition for use and removing the reusable multi-use surgical medical device from the solution and releasing residual solution by manual wringing. The method further includes hydrating a tissue or organ of a patient by arranging the conditioned reusable multi-use surgical medical device adjacent to the organ or tissue during the medical procedure.

One embodiment is directed towards a method for performing a medical procedure with a reusable multi-use surgical medical device including providing the reusable multi-use surgical medical device comprising an hydrophilic open-celled reticulated foam material having an ultra-low number of particles, a plurality of radiopaque (RO) ink markers adhered to a surface of the reticulated foam material configured to be visible under an imaging device at various orientations, and having a bacterial endotoxin level below at least 20.0 EU/medical device. The method further includes initially applying a solution to the reusable multi-use surgical medical device to condition it for use. The method further includes removing the reusable multi-use surgical medical device from the solution and releasing residual solution by manual wringing. The method further includes arranging the reusable multi-use surgical medical device under a medical instrument to protect and hydrate the tissue or organ of a patient by during the procedure.

One embodiment is directed towards a medical kit including one or more medical devices as described with reference to any embodiment herein and instructions for use.

In one embodiment, the medical device is used as an absorbent sponge in a variety of medical procedures. It can be rinsed in saline and fluid or blood can be squeezed out. A variety of different solutions may be utilized with the medical device such as antibiotic solution, antiseptics, coagulants, anticoagulants, or other solutions.

In one embodiment, the medical device can be used to estimate blood loss and/or body fluids of a patient during a trauma or procedure. For example, the medical device can be used to absorb blood and/or body fluids of a patient during trauma or procedure. Next, the device is squeeze or wrung out into a measuring bowl or other measuring apparatus and the volume of retrieved blood and/or body fluids is obtained. The measured volume of blood and/or body fluid can then be used to estimate the blood loss and/or body fluids of the patient.

In one embodiment, a suture may be placed through the medical device.

In one embodiment, the medical device can be used in endoscopic and laparoscopic procedures. It can be placed, advanced and retrieved through trocars due to its conformability and flexibility and it is also resilient to avoid fragmentation and degradation.

In one embodiment, the medical device is hydrated with techniques known in the art and used to prevent tissues from drying out during a procedure.

In one embodiment, the medical device is used for wound packing and can pack off bleeding and is also used as trauma and wound dressing.

In one embodiment, the medical device can be used to protect tissues from instrument trauma, e.g., it can be used between a retractor and the tissue. Moreover, it can be hydrated with any pharmacologic agent described herein to also prevent tissue from drying out during procedures.

In one embodiment, the medical device can be used on the patient for cleaning, wiping, absorbing, and packing of a wound or cavity.

In one embodiment, the medical device can be used in dental or oral surgery procedures.

In one embodiment, the medical device can be used in veterinary applications or procedures.

In embodiment, the medical device can be used with a variety of different medical procedures for cleaning, wiping, absorbing, hydrating and other uses. The variety of different medical disciplines it can be used in include at least one or more of general surgery, coronary artery bypass graft (CABG) procedures, thoracic procedures, colorectal procedures, gastrointestinal procedures, trauma procedures, plastic surgery procedures, orthopedic procedures, neurosurgery procedures, burn surgeries and procedures, e.g., skin grafts, eye surgery procedures, robotic procedures, and a variety of other specialties and the like.

In one embodiment, the medical device can be used with an endoscope as an endoscopic sponge for cleaning or inserting through or into portions of the endoscope or its endoscope attachments.

In one embodiment, the medical device can be irrigated and suctioned through given the porosity, cell structure and pore size. It absorbs better than related art devices and is non-abrasive. It can also be used as a platform to hold up nerves, spinal cords, other medical devices, and instruments. For example, cannulas or needles for suturing can be inserted into the medical device to temporality secure them.

In one embodiment, the medical device can be used as a makeup remover or for other non-medical uses.

Reference will now be made in detail to an embodiment of the present invention, example of which is illustrated in the accompanying drawings.

FIG. 1 illustrates a magnified view of a cellulose laparotomy pad for the absorption of discharges according to the related art.

Referring to FIG. 1, the magnified view is achieved with an electron microscope and the laparotomy pad is generally represented with reference to number 100. As shown, the laparotomy pad 100 is manufactured with cellulose and includes a number of bundled fibers 102 and loose fibers 104 and other contaminants. The fibers, lint and other contaminants can be described as particulates or quantified. Referring to Table 1 and the Example section the medical device 100 has a high number of particulates as compared to medical device described with reference to several embodiments herein. This high number of particulates is believed to cause various medical complications, e.g., post-operative complications, SSIs, HAIs, and other complications described herein. These complications increase medical costs and overall health care costs significantly. Moreover, this device 100 is not reusable or washable leading to increased cost of a procedure to dispose of medical waste.

FIG. 2 illustrates a magnified view of a cellulose gauze for use with medical procedures according to the related art.

Referring to FIG. 2, the magnified view of a cellulose gauze device 200 is achieved with an electron microscope. The device 200 is manufactured with cellulose and the fibers 202 can be seen. The fibers 202, lint and other contaminants can be described or quantified as particulates. Referring to Table 1 and the Example section the device 200 has a high number of particulates as compared to the medical device described with reference to several embodiments herein. This high number of particulates is believed to cause various medical complications, e.g., post-operative complications, SSIs, HAIs, and other complications described herein. These complications increase medical costs and overall health care costs significantly. Moreover, this device 100 is not reusable or washable during a procedure.

FIG. 3 illustrates a non-magnified view of a non-adherent pad according to the related art. FIG. 4 illustrates a magnified view of a non-adherent pad according to the related art.

Referring to FIGS. 3-4, the non-magnified view and magnified with an electron microscope of a non-adherent pad 300, e.g., a Telfa pad. As shown, the non-adherent pad 300 is manufactured from cellulose and includes a number of fibers 302, 304 and 306 through a layer 308. The device 300 has fibers 302, 304 and 306, lint and other contaminants can be described or quantified as particulates. Referring to Table 1 and the Example section the device 300 has a high number of particulates as compared to the medical device described with reference to several embodiments herein. This high number of particulates is believed to cause various medical complications, e.g., post-operative complications, SSIs, HAIs, and other complications described herein. These complications increase medical costs and overall health care costs significantly. Moreover, this device 100 is not reusable or washable.

FIG. 5 illustrates a magnified view of a medical device according to an implementation of the present disclosure.

Referring to FIG. 5, the magnified view of the medical device 500 is achieved with an electron microscope. As shown, the medical device 500 is constructed from an open celled foam material of reticulated foam made from a material described herein. The foam material includes a number of open cells 502. The foam material is described in greater detail herein and can be either hydrophilic or hydrophobic. The open cell foam 500 is permeable to fluids and can be suctioned through. The open cell foam has a plurality of pores 502 and the pore size can be in a range from about 50 ppi to about 85 ppi or greater.

The device 500 has ultra-low number of particulates as compared to the related art devices as shown in Table 1 and the Example section. The medical device 500 does not contain cellulose, lint, latex, bisphenol A (BPA), or di(2-ethylhexyl) phthalate (DEHP). In a preferred embodiment, the device does not contain butyl benzyl phthalate (BBP), dibutyl phthalate (DBP), or diisobutyl phthalate (DIBP). The device has an endotoxicity level that is below 20.0 EU/device, and in a preferred embodiment, the endotoxicity level is below about 7.0 EU/device.

The device 500 is configured to reduce post-operative complications, SSI and HAI. These complications increase medical costs and overall health care costs significantly. The device 500 is reusable and washable during a medical procedure, thereby it is useable.

Figure 6:
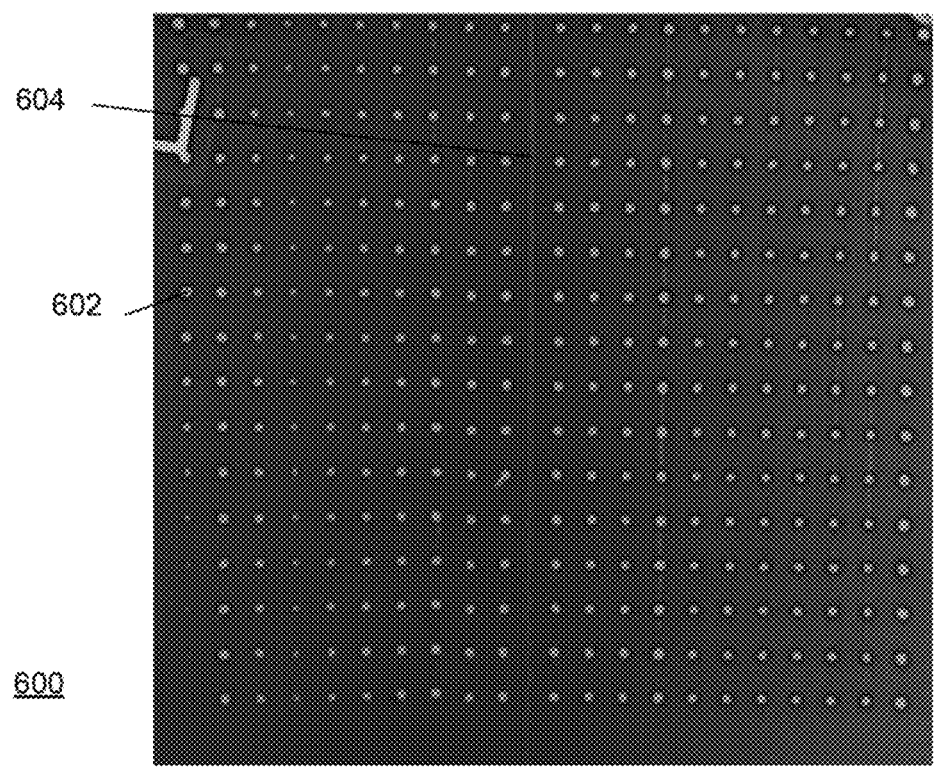
FIG. 6 illustrates an exemplary x-ray view of a medical device with imaging markers according to an implementation in a first orientation of the present disclosure.
Figure 7:
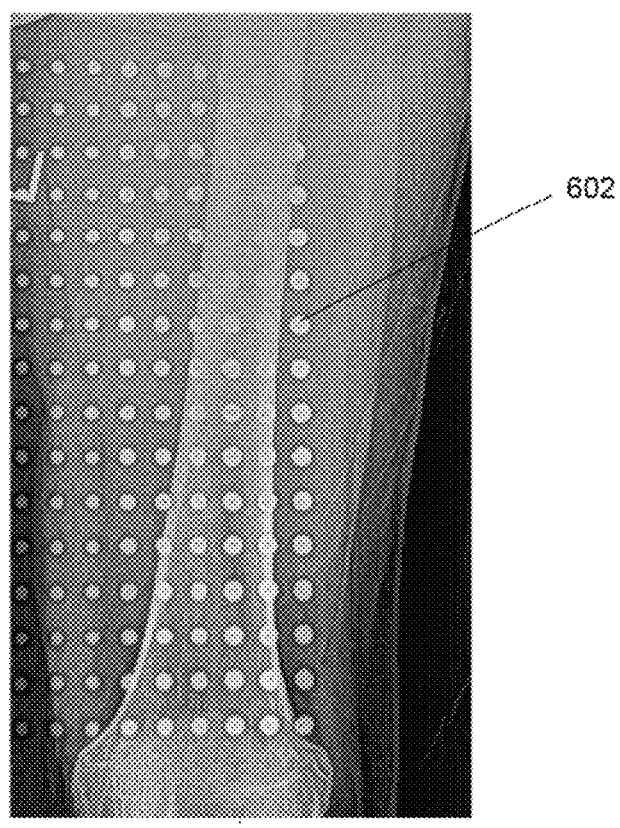
FIG. 7 illustrates an exemplary x-ray view of the medical device of FIG. 6 with imaging markers in a second orientation.
Figure 8:
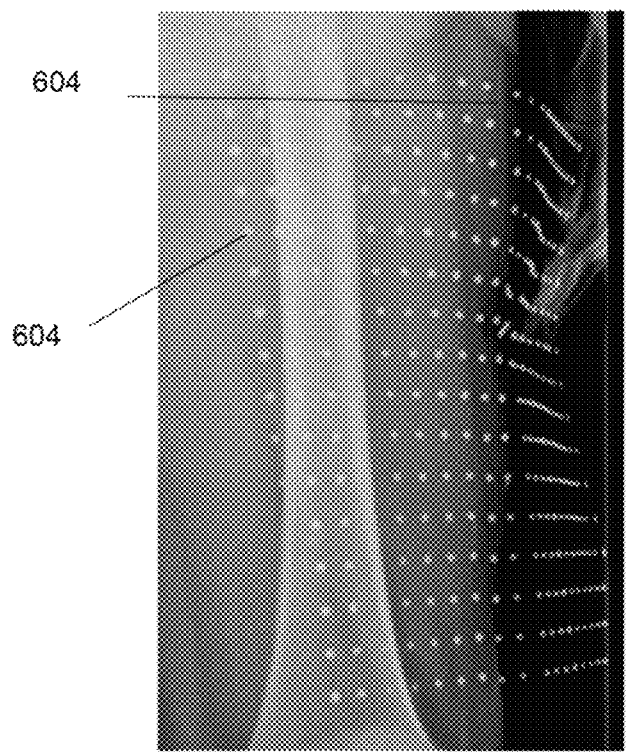
FIG. 8 illustrates an exemplary x-ray view of the medical device of FIG. 6 with imaging markers in a third orientation.

FIG. 6 illustrates an exemplary x-ray view of a medical device 600 with imaging markers according to an implementation in a first orientation of the present disclosure. FIG. 7 illustrates an exemplary x-ray view of the medical device of FIG. 6 with imaging markers in a second orientation. FIG. 8 illustrates an exemplary x-ray view of the medical device of FIG. 6 with imaging markers in a third orientation.

Referring to FIG. 6-8, the medical device 600 includes a radiopaque (RO) imaging marker including a plurality of RO ink markers 602 and RO string marker 604 that is sewn into the foam material. As shown, the RO string marker 604 is hard to see as compared to the RO ink markers 602. The RO ink markers 602 in this embodiment have different diameters arranged in a grid pattern. Optionally and/or alternatively, the array pattern can be uniform or non-uniform.

The diameter of the RO ink markers 602 can have a dimension in a range from 0.5 mm to about 10 mm or greater or less. In a preferred embodiment, the diameter is in a range from 3 mm to about 5 mm. The RO ink markers are applied with a printed, deposited, or other application technique described herein. The RO ink is radiopaque or an echogenic ink that is configured to be detectable or visible under ultrasound or other visualization instrument, x-ray imaging, ultrasound imaging device, or other imaging device.

The RO ink markers 602 can have the same diameters or different diameters. The RO ink markers 602 can be applied in any geometric configuration, e.g., triangle, circle, square or rectangle. The RO ink can be formed on a surface of the foam material or embedded into a volume of the foam. The RO ink can have a thickness in a range from about 50 μm or greater. When the RO ink is embedded into the foam it can be done in a column type pattern for even more enhanced visibility when the device is in different orientations.

The RO markers 602 are readily visible at different orientations of the x-ray imaging. More specifically, FIG. 6 is an x-ray image of the medical device 600 at anterior projection (AP) orientation, FIG. 7 is an x-ray image of the medical device 600 at an AP projection, and FIG. 8 is an image of the medical device 600 at an right anterior oblique (RAO) projection. Referring to FIG. 8, the RO ink markers 602 are clearly show in two separate orientations, e.g., AP and RAO. As shown and described herein the RO ink markers 602 have enhanced visualization as compared to the RO string marker 604.

Figure 9:
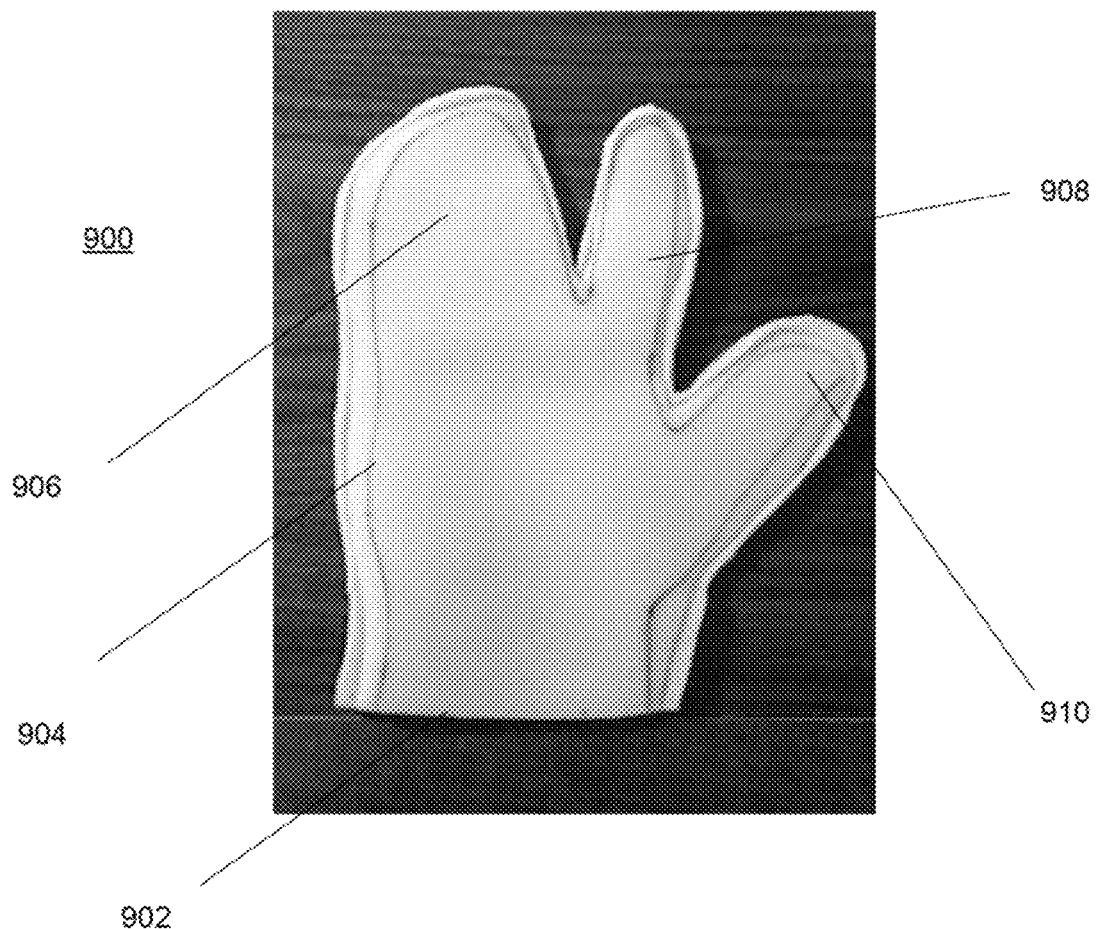
FIG. 9 illustrates the medical device arranged in a glove configuration according to an implementation of the present disclosure.

Referring FIG. 9, the medical device is generally depicted with reference to 900. The device 900 includes a hydrophilic foam material as described herein. The device 900 is configured as a glove or claw glove with a slot 910 for a thumb, an index finger slot 908 and the remaining fingers slot 906.

Optionally and/or alternatively, the device 900 may be configured only to cover a finger, or more than one finger and thumb. In this embodiment, the device 900 has an opening 902 to receive a portion of the hand. The device 900 is constructed from a foam material as described herein as a first pattern and a second pattern joined together with an attachment mechanism 904, e.g., suture, adhesive, staples, heat bonding and combinations of the same or the like.

Optionally and/or alternatively, the device 900 includes RO imaging markers as described herein. The device 900 can be used with any surgical procedures described herein.

Figure 10:
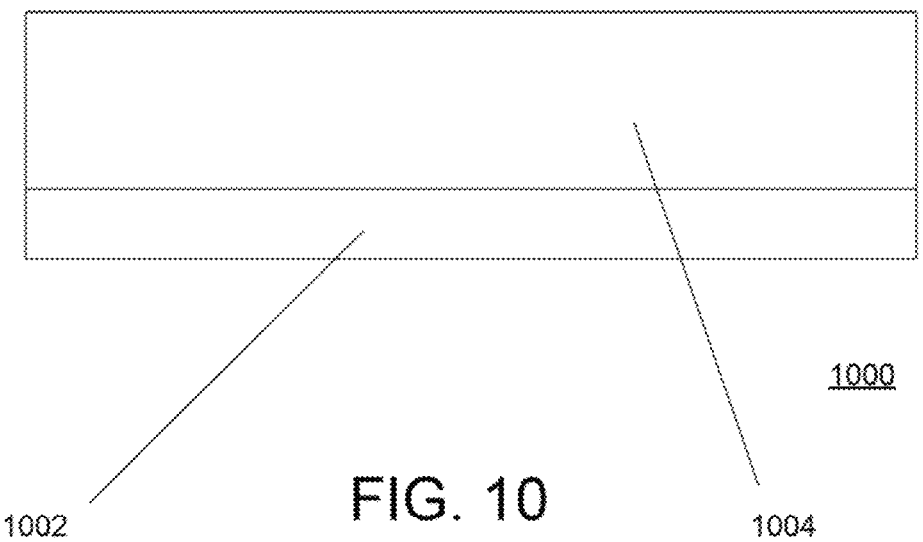
FIG. 10 illustrates an exemplary view of a medical device according to another implementation of the present disclosure.

FIG. 10 illustrates an exemplary perspective view of a medical device according to an implementation of the present disclosure.

Referring FIG. 10, the medical device is generally depicted with reference to 1000. The device 1000 includes a foam material 1004 non-releasably attached to the substrate 1002. The substrate 1002 may be any material e.g., plastic, thermoplastic, paper, cardboard, combination of the same or the like or any rigidity, e.g., stiff, flexible, etc. In this embodiment, the substrate 1002 includes a rigid thermoplastic material adhered to the 1004 with one or more of heat, adhesive, suture, staple, and the like. The foam material 1004 may be any material described herein. The substrate is configured to increase the rigidity of the foam material 1004.

The device 1000 can be used with any surgical procedures described herein.

Figure 11:
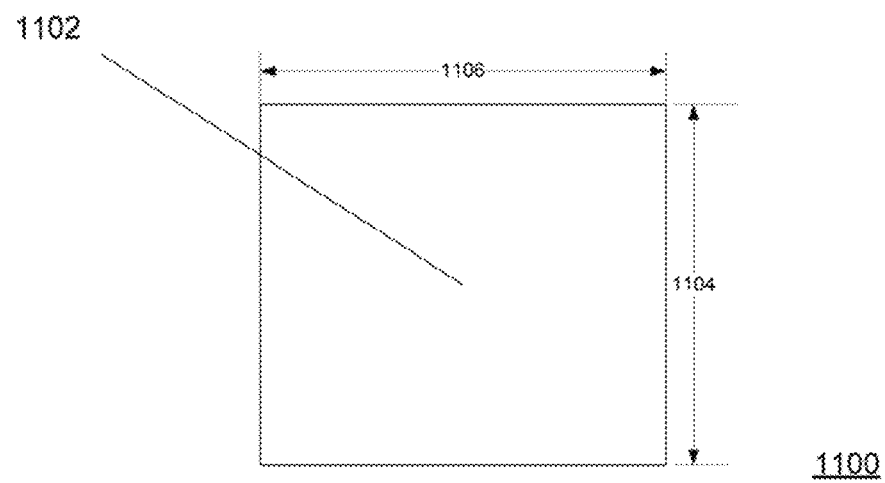
FIG. 11 illustrates an exemplary view of a medical device according to another implementation of the present disclosure.

FIG. 11 illustrates an exemplary perspective view of a medical device according to an implementation of the present disclosure.

Referring FIG. 11, the foam medical device is generally depicted with reference to 1100. The device 1100 is configured as a foam material 1102 has described herein. In this embodiment, the device is a square geometric configuration with a length 1104, width 1106 and thickness (not shown) into the substrate. The thickness (not shown) may be in a range from about ⅛ inch or greater, e.g., ⅛ inch to about 3 inch or greater, the length by about ⅛ inch to about 12 inch or greater, and the width in a range from about ⅛ inch to about 12 inch or greater.

Optionally and/or alternatively, the device 1100 has one or imaging markers described herein. The device 1100 can be used with any surgical procedures described herein.

Figure 12:
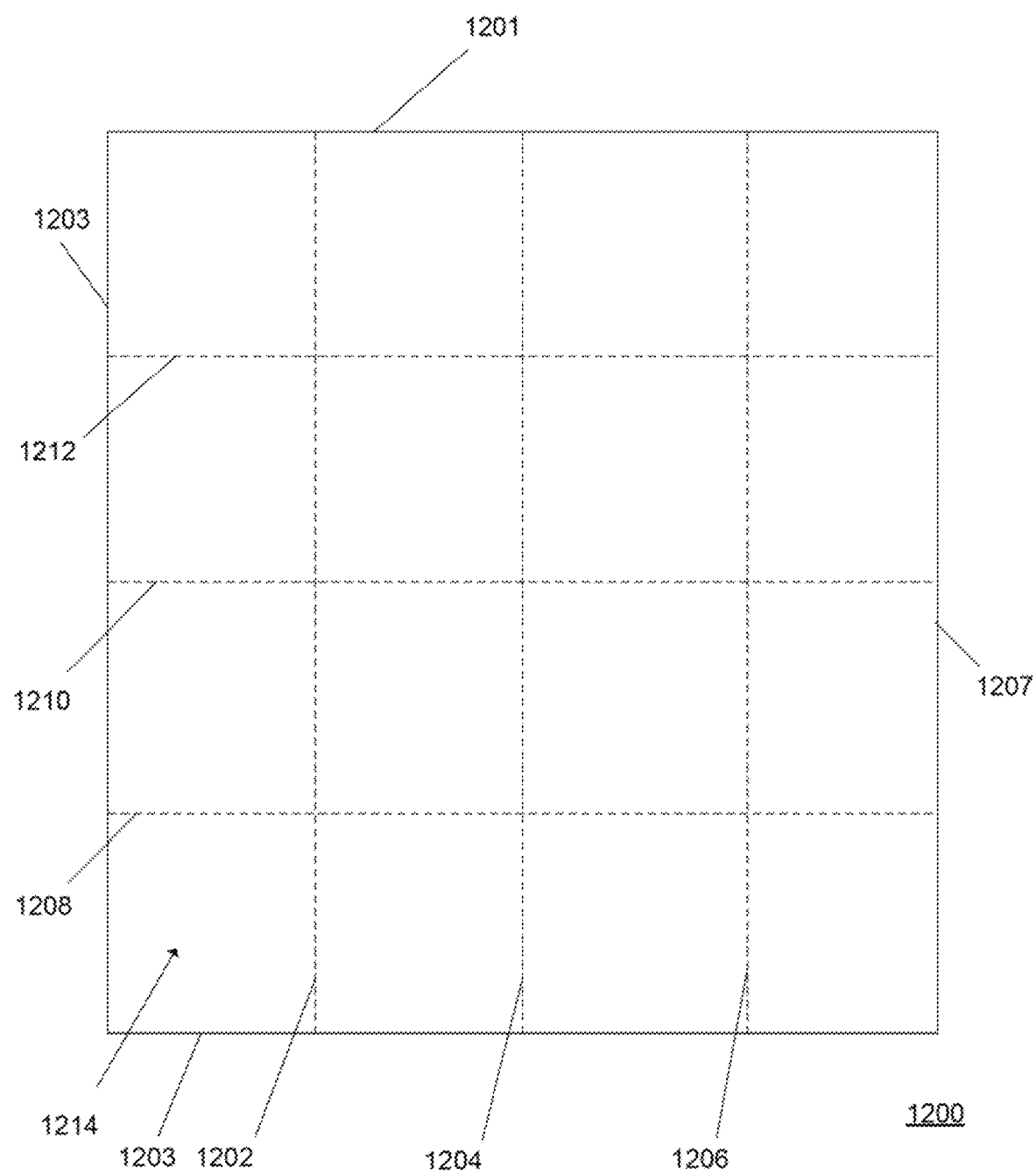
FIG. 12 illustrates an exemplary method of using a medical device according to another implementation of the present disclosure.

FIG. 12 illustrates an exemplary perspective view of a medical device according to an implementation of the present disclosure.

Referring to FIG. 12, the device 1200 is configured as a sheet of foam material having top 1201, a bottom 1203, a first side 1205 and a second side 1207. Perforations are arranged through a thickness of the foam. The perforations are arranged as a vertical line of perforations 1202, 1204, and 1206 and perforations are arranged in horizontal lines of perforations 1208, 1210, 1212. The perforations are configured through or partially through the foam material and are configured to separate the material into medical devices 1214 of predetermined sizes. The perforations can be in any pattern or orientation to create medical devices of different geometries, e.g., circle pattern, square pattern, triangle pattern, rectangle pattern and the like. The perforations are further configured through the material to allow for easy separation into a predetermined sections 1214. Optionally and/or alternatively, the device 1100 has one or imaging markers described herein.

Figure 13:
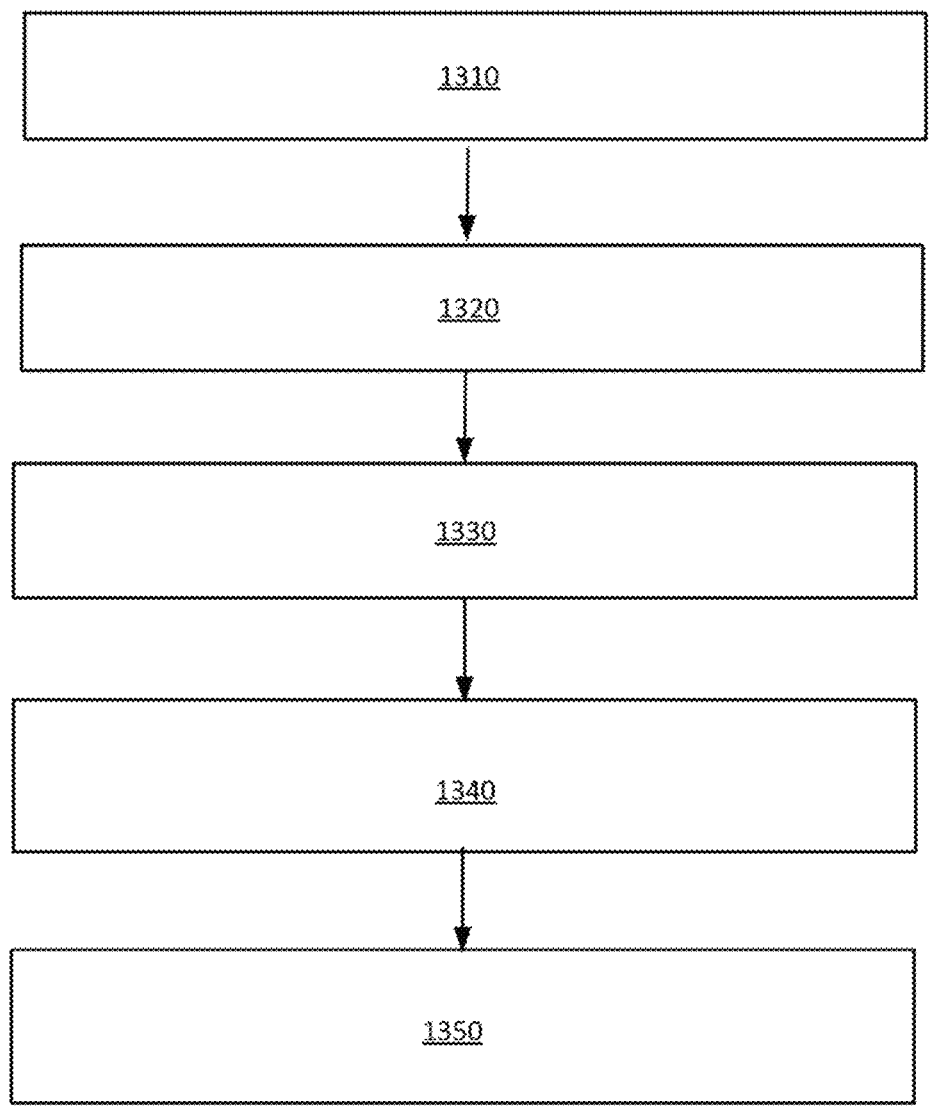
FIG. 13 illustrates an exemplary method of using a medical device according to another implementation of the present disclosure.

FIG. 13 illustrates an exemplary method of using a medical device according to another implementation of the present disclosure.

A method for performing a medical procedure with a reusable multi-use surgical medical device is generally described with reference to number 1300. In step 1310 the user provides the reusable multi-use surgical medical device as described in any of the embodiments or examples herein. In step 1320 the user applies a solution to the reusable multi-use surgical medical device to condition for use by arranging the medical device in a bowl containing the solution. The solution can be any solution described herein, e.g., saline or water. In step 1330 the user removes the reusable multi-use surgical medical device from the solution and releases residual solution by manual wringing, e.g., with hands. In step 1340 the user uses the conditioned reusable multi-use surgical medical device during a surgical procedure. The surgical procedure can be any surgical procedure described herein. In step 1350 the user returns the now-used reusable multi-use surgical medical device to the bowl containing the solution to clean and rinse it. Optionally, in step 1360, the user can repeat any of the steps 1320, 1330, 1330, 1340 and 1350, as necessary.

Figure 14:
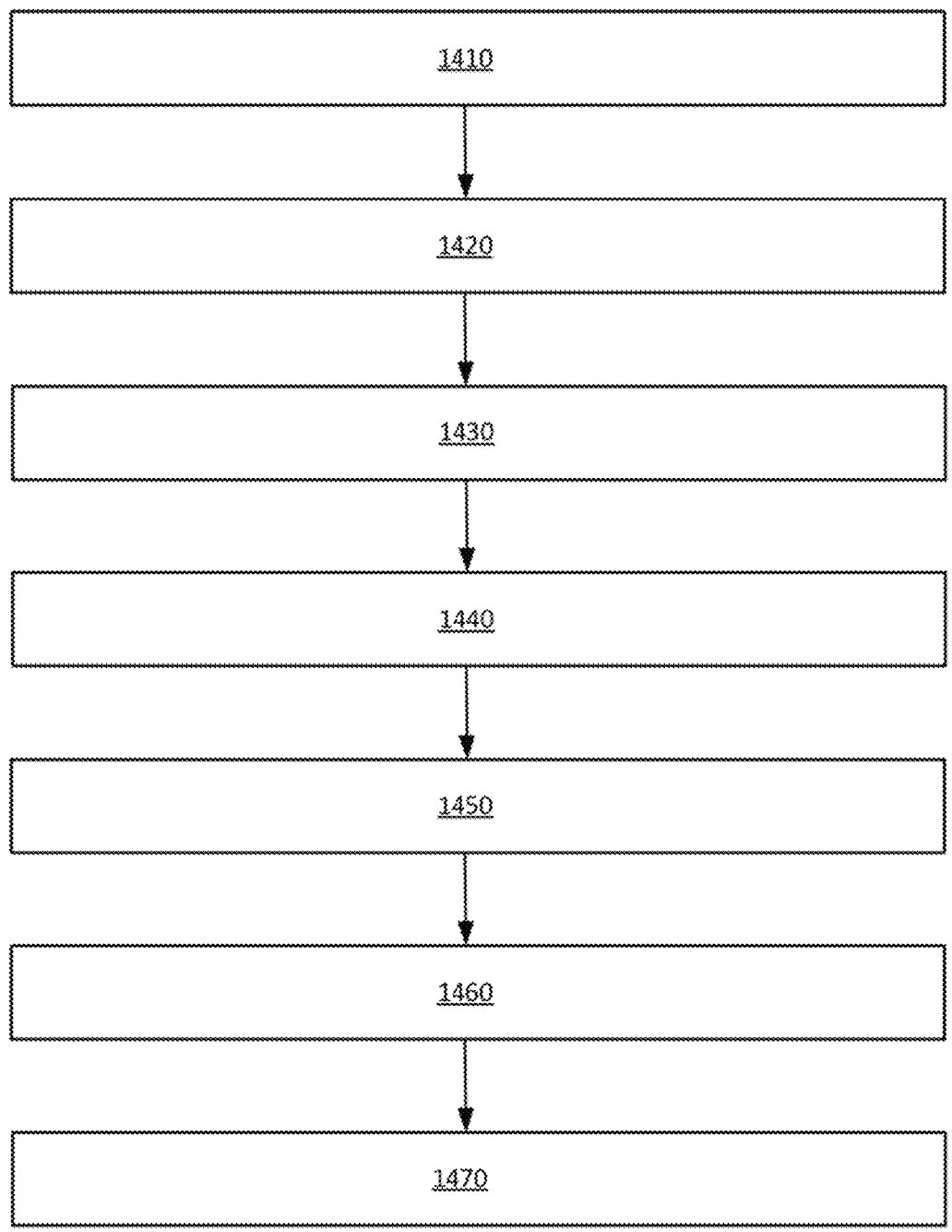
FIG. 14 illustrates an exemplary method of using a medical device according to another implementation of the present disclosure.

FIG. 14 illustrates an exemplary method of using a medical device according to another implementation of the present disclosure.

A method for performing a medical procedure with a reusable multi-use surgical medical device is generally described with reference to number 1400. In step 1410 the user provides the reusable multi-use surgical medical device as described in any of the embodiments or examples herein. In step 1420 the user applies a solution to the reusable multi-use surgical medical device to condition for use by arranging the medical device in a bowl containing the solution. The solution can be any solution described herein, e.g., saline or water. The reusable multi-use surgical medical device is completely hydrated in the bowl. In step 1430 the user removes the reusable multi-use surgical medical device from the solution and releases residual solution by manual wringing, e.g., with hands. In step 1440 the user manipulates the device by arranging it into a proximal end of a trocar. In step 1450 a blunt grasping instrument is used to push the conditioned multi-use surgical medical device through a lumen of the trocar into a bowl, e.g., a catch basin. In step 1460 after the reusable multi-use surgical medical device is used the conditioned reusable multi-use surgical medical device returns to its normal shape. Optionally, in step 1470 the user returns the now-used reusable multi-use surgical medical device to the bowl containing the solution to clean and rinse it. Optionally, in step 1480 the user can with the blunt grasping instrument push the used and reconditioned multi-use surgical medical device through a lumen of the trocar into a bowl, e.g., a catch basin. Any of these steps may be repeated as desired.

EXAMPLE SECTION

The following examples are intended to be illustrative only and are not intended to limit the scope of the invention to only the constructions described by these examples.

Example 1

A medical device having a hydrophobic foam material was tested having a length of about 3 inches, thickness of about 0.25 inches and width dimension of about 3 inches. The device was first submerged in 100 ml of a low particulate water (LPW) that is filtered with a twin 0.1 micron filter system and then squeezed to remove saline and this step was repeated three times. Next, the device was placed in a testing solution of LPW and tested for particulates. This device was tested by Nelson Laboratories for particulate matter as set forth in Appendix A. Particulate matter is defined in the USP as extraneous, mobile, undissolved substances, other than gas bubbles, unintentionally present in a solution (or in/on a device). All test method acceptance criteria were met. Testing was performed in compliance with US FDA good manufacturing practice (GMP) regulations 21 CFR Parts 210, 211 and 820.

Light Obscuration was done with testing performed using the HIAC Royco Liquid Particle Counting System (LPC), Model #9703. The counter detects and sizes particles using a light-obscuration sensor. The LPC's sensor was calibrated by the manufacturer using polystyrene latex particles from 2 µm to 100 µm. Testing was conducted to ensure compliance with the applicable standard listed in the interpretation of results section.

Results are shown as values rounded to the nearest whole number. If present, results reported as "0" do not necessarily indicate that zero particles were detected.

Test Method Acceptance Criteria: Light Obscuration (LO): The environment control must have no more than a total of 25 particles ≥10 µm when adding the counts of all five aliquots (25 mL total). The positive control must exceed the USP <788> large volume criteria.

Interpretation of Results: Light Obscuration: USP <788> and EP 2.9.19 Requirements: There are no USP or EP specifications for particulate matter found in/on medical devices. The results are shown in Tables 2, 3, and 4.

TABLE 2

Light Obscuration/Test Article
Particles/Test Article

| Particle Size [µm] | Number Particles [particles/cm$^2$] |
|---|---|
| ≥10 | 3,334 |
| ≥25 | 67 |

TABLE 3

Control

| Particle Size [µm] | Number Particles |
|---|---|
| Environment Control (Particles/25 mL) | |
| ≥10 | 6 |
| ≥25 | N/A |
| Positive Control (Particles/mL) | |
| ≥10 | 1,149 |
| ≥25 | 127 |

TABLE 4

Light Obscuration/Test Article

| Volume | ≥10 | ≥25 |
|---|---|---|
| Large | Particles/mL | Particles/mL |
| Small | Particles/Container | Particles/Container |

Example 2

Medical devices having an open-celled foam material described herein having a length of 3 inches, a thickness of 0.25 inches and a width dimension of 3 inches and a medical device having a length of 9 inches, a length of 9 inches and a thickness of 0.25 inches were tested for endotoxicity levels.

Each of the devices were tested by a lab. The Bacterial Endotoxins Test (BET), or Limulus Amebocyte Lysate (LAL) test, is an invitro assay to detect and quantify bacterial endotoxin, a component of the cell wall of Gram negative bacteria. Standard controls and a positive product control (PPC) demonstrate a compliant assay. A PPC recovery within the 50%-200% range indicates that the test solution is free of interfering factors given the specific conditions of the test. If applicable, dilutions are calculated into the reported endotoxin level. All test method acceptance criteria were met. The testing was conducted in accordance with the following regulatory documents: ANSI/AAMI ST72:2011/(R)2016, USP<161>, USP <85>, EP 2.6.14, and JP 4.01. Testing was performed in compliance with US FDA good manufacturing practice (GMP) regulations 21 CFR Parts 210, 211 and 820. The results are shown in Table 5.

TABLE 5

Results

| Sample Size [inches] | Type | Extraction Volume | Detected Endotoxin | PPC Recovery | Spike Recovery (Inhibition/Enhancement) |
|---|---|---|---|---|---|
| 3 × 3 × 0.5 | hydrophobic | 156 mL/device | 0.00500 EU/mL or 0.781 EU/device | | 81% |
| 9 × 9 × 0.5 | hydrophilic | 1009 mL/Device | 0.00613 EU/ml or 6.19 EU/device | 129% | n/a |

As shown from above, the device is usable for various medical applications including cerebrospinal fluid contact situations. The standard for finished medical devices is an endotoxin limit not more than 20.0 EU/device. In addition, the endotoxin limit for medical devices in contact with cerebrospinal fluid is not more than 2.15 EU/device and the endotoxin limit for medical devices in contact with intraocular ophthalmic devices is not more than 0.2 EU/device.

Example 3

A total of eight medical device specimens were tested as shown in Table 6 for abrasion resistance. The Martindale Abrasion Test under the ASTM International (formerly the American Society for Testing and Materials) D49 66-Standard Test Method for Abrasion Resistance of Textile Fabrics (Martindale Abrasion Tester Method) was used to test a medical device's resistance to abrasion. The medical device's ability to resists abrasion, tears and punctures is particularly important to avoid contamination to the patient from the medical device.

In this Example, the testing was performed on a Martindale tester manufactured by James H. Heal & Co. Ltd and results are in Table 6. A total of 8 specimens were tested and details can be found in the following table. The specimens were loaded per the tester instructions and each specimen had a pressure of 9 kpa and #10 duck cloth for the abradant. No testing anomalies were noted. Foam samples showed no visible wear during the test. A small amount of fibers from the duck cloth were seen in the pores of the foam samples at 16,000 cycles. At no time did any of the foam transfer to the abradant. Gauze samples transferred fibers to the abradant at 2,000 cycles. At 4,000 cycles, the gauze disintegrated, and the testing of this sample was terminated at 6,000 cycles. Lap sponge samples began shedding minor fibers at 4,000 cycles. At 11,000 cycles, an excessive amount of white powder was observed on the abradant and abradant holder. At 14,000 cycles, pilling began to occur. Testing was stopped at 15,000 cycles.

TABLE 6

Abrasion Resistance Summary

| Sample No. | Nature | Size [inches] | Cycles | Conditions |
|---|---|---|---|---|
| 1 | Hydrophilic Foam | ¼ | 25,000 | 22° C./50% R.H. |
| 2 | Hydrophilic Foam | ¼ | 25,000 | 22° C./50% R.H. |
| 3 | Hydrophilic Foam | ½ | 25,000 | 22° C./50% R.H. |
| 4 | Hydrophilic Foam | ½ | 25,000 | 22° C./50% R.H. |
| 5 | Gauze white | — | 6,000 | 22° C./50% R.H. |
| 6 | Gauze white | — | 6,000 | 22° C./50% R.H. |
| 7 | Lab Sponge - white | — | 15,000 | 22° C./50% R.H. |
| 8 | Lab Sponge - white | — | 15,000 | 22° C./50% R.H. |

Example 4

A number of laundered medical devices were tested for particulates with results shown in Table 7. Each device was laundered in an aqueous solution of low particulate water (LPW) to reduce manufacturing particulates. Liquid Particle Counting (LPC) system and processing was used to determine a particulate count.

TABLE 7

Particle Summary

| Trial | Foam Material Type | Size [inches] | No. of particles ≥ 5 μm [particles/cm$^2$] |
|---|---|---|---|
| 1 | Hydrophilic | 0.25 × 0.5 × 3 | 6,200 |
| 2 | Hydrophilic | 0.25 × 0.5 × 3 | 9,187 |
| 3 | Hydrophilic | 0.25 × 0.5 × 3 | 8,786 |
| Average | | | 8,058 |
| 1 | Hydrophilic | 0.25 × 1 × 3 | 9,574 |
| 2 | Hydrophilic | 0.25 × 1 × 3 | 9,718 |
| 3 | Hydrophilic | 0.25 × 1 × 3 | 9,276 |
| Average | | | 9,523 |
| 1 | Hydrophilic | 0.25 × 1 × 3 | 9,574 |
| 2 | Hydrophilic | 0.25 × 1 × 3 | 9,718 |
| 3 | Hydrophilic | 0.25 × 1 × 3 | 9,276 |
| Average | | | 9,523 |
| 1 | Hydrophilic | 0.25 × 3 × 3 | 6,200 |
| 2 | Hydrophilic | 0.25 × 3 × 3 | 9,187 |
| 3 | Hydrophilic | 0.25 × 3 × 3 | 8,786 |
| Average | | | 8,058 |
| 1 | Hydrophilic | 0.25 × 3 × 9 | 14,668 |
| 2 | Hydrophilic | 0.25 × 3 × 9 | 9,061 |
| 3 | Hydrophilic | 0.25 × 3 × 9 | 10,838 |
| Average | | | 11,523 |
| 1 | Hydrophilic | 0.25 × 6 × 9 | 13,295 |
| 2 | Hydrophilic | 0.25 × 6 × 9 | 16,513 |
| 3 | Hydrophilic | 0.25 × 6 × 9 | 14,436 |
| Average | | | 14,748 |
| 1 | Hydrophilic | 0.25 × 9 × 9 | 8,257 |
| 2 | Hydrophilic | 0.25 × 9 × 9 | 7,104 |
| 3 | Hydrophilic | 0.25 × 9 × 9 | 7,694 |
| Average | | | 7,694 |
| 1 | Hydrophilic | 0.5 × .5 × 3 | 10,957 |
| 2 | Hydrophilic | 0.5 × .5 × 3 | 8,564 |
| 3 | Hydrophilic | 0.5 × .5 × 3 | 9,012 |
| Average | | | 9,511 |
| 1 | Hydrophilic | 0.5 × 1 × 3 | 6,391 |
| 2 | Hydrophilic | 0.5 × 1 × 3 | 5,744 |
| 3 | Hydrophilic | 0.5 × 1 × 3 | 5,417 |
| Average | | | 5,851 |
| 1 | Hydrophilic | 0.5 × 3 × 3 | 43,408 |
| 2 | Hydrophilic | 0.5 × 3 × 3 | 27,049 |
| 3 | Hydrophilic | 0.5 × 3 × 3 | 14,685 |
| Average | | | 28,380 |
| 1 | Hydrophilic | 0.5 × 3 × 9 | 5,604 |
| 2 | Hydrophilic | 0.5 × 3 × 9 | 6,256 |
| 3 | Hydrophilic | 0.5 × 3 × 9 | 3,762 |
| Average | | | 5,207 |
| 1 | Hydrophilic | 0.5 × 6 × 9 | 5,856 |
| 2 | Hydrophilic | 0.5 × 6 × 9 | 7,621 |
| 3 | Hydrophilic | 0.5 × 6 × 9 | 7,696 |

TABLE 7-continued

Particle Summary

| Trial | Foam Material Type | Size [inches] | No. of particles ≥ 5 μm [particles/cm$^2$] |
|---|---|---|---|
| Average | | | 7,058 |
| 1 | Hydrophilic | 0.5 × 9 × 9 | 10,337 |
| 2 | Hydrophilic | 0.5 × 9 × 9 | 9,957 |
| 3 | Hydrophilic | 0.5 × 9 × 9 | 6,946 |
| Average | | | 9,080 |

Example 5

Medical device specimens were tested for cytotoxicity as shown in Table 8. A cytotoxicity test using the MEM elution method was utilized. The specimens were open-celled foam each having a blue thread sewn into across each sample. The blue thread included radiopaque (RO) material. The test method was ISO 10993-5 biological evaluation of method medical device-Part 5: Test for in vitro cytotoxicity Test on Extracts. The reagent control was 1×MEM composition: 92% Gibco MEM Earle's salts, 5% fetal bovine serum, 1% antibiotics (10,000 units/mL, Penicillin G sodium and 10,000 μg/mL Streptomycin sulfate in 0.85%), Sodium pyruvate 1% (100 mM) and 1% (200 mM) L-glutamine. The negative control was high density polyethylene (HDPE). The positive control was 0.1% ZDEC polyurethane film (RM-A). The tissue code L929, (Mouse fibroblast cells, ATCC CCL-1, NCTC 929).

The test preparation was based on USP ratio of 60 cm$_2$: 20 mL. The reagent control preparation used a medium test specimen as reagent control. The negative control preparation, was high density polyethylene (HDPE), was used as a negative control material that was tested in accordance with ISO 10993-5:2009(E). The positive control preparation, was 0.1% ZDEC polyurethane film (RM-A), was used as a positive control in accordance with ISO 10993-5:2009(E). based on the SP ration of 60 cm$_2$: 20 mL.

The method utilized was cell suspension of 2×10$^5$ cells/mL L929 in MEM completed medium was feed into the 6 well plate each 3 ml per well. It was incubated at 37° C., 5% CO2 to obtain confluent monolayer prior to testing. The MEM completed medium was replaced with the extracts of test sample, negative control, and positive control. After incubation, the cells were examined microscopically for cytotoxic response. Observation for the test extract and negative control were conducted at 24 hours, 48 hours, and 72 hours of incubation. The positive control well was observed at 24 hours of incubation. To determine any change in cell morphology clearly, scoring for cytotoxicity was based on the criteria. Table 7 shows the results.

TABLE 8

Cytotoxicity Test Results

| Sample Size | Confluent Monolayer | % show changes in morphology | % cell without granulation and rounding | % Lysis | Cytotoxicity Score | Interpretation |
|---|---|---|---|---|---|---|
| 1 | (+) | 0 | 0 | 0 | 0 | Non-toxic |
| 2 | (+) | 0 | 0 | 0 | 0 | Non-toxic |
| 3 | (+) | 0 | 0 | 0 | 0 | Non-toxic |
| 4 | (+) | 0 | 0 | 0 | 0 | Non-toxic |
| 5 | (+) | 0 | 0 | 0 | 0 | Non-toxic |
| 6 | (+) | 0 | 0 | 0 | 0 | Non-toxic |
| 7 | (+) | 0 | 0 | 0 | 0 | Non-toxic |
| 8 | (+) | 0 | 0 | 0 | 0 | Non-toxic |
| 9 | (+) | 0 | 0 | 0 | 0 | Non-toxic |
| 10 | (+) | 0 | 0 | 0 | 0 | Non-toxic |
| 11 | (+) | 0 | 0 | 0 | 0 | Non-toxic |
| Reagent Control | (+) | 0 | 0 | 0 | 0 | Non-toxic |
| Negative Control | (+) | 0 | 0 | 0 | 0 | Non-toxic |
| Positive Control | (−) | 100 | 100 | 100 | 4 | Toxic |

As shown in Table 7 the medical devices were non-toxic and did not have cytotoxicity. A value of 0 was no reactivity and conditions of all cultures was discrete intracytoplasmic granules, no cells lysis, no reduction of cell growth. A value of 4 is severe reactivity and conditions of all cultures was nearly complete or complete destruction of the cell layers.

Example 6

In this Example 6, the number of particles associated with medical devices as identified in Table 9 were tested with a testing lab. Each of the medical devices identified as having hydrophilic foam material were laundered in an aqueous solution to remove manufacturing particulates prior to testing. The number of particles were measured with Light Obscuration (LO) system and techniques as known in the art and as described with reference to Example 1.

TABLE 9

Particulate Summary

| Foam Material Type* | Size [inches] | No. of particles ≥5 μm [particles/cm²] | No. of particles ≥10 μm [particles/cm²] | No. of particles ≥25 μm [particles/cm²] | No. of particles ≥50 μm [particles/cm²] | No. of particles ≥100 μm [particles/cm²] | Test Method |
|---|---|---|---|---|---|---|---|
| Hydrophilic | 3 × 3 × 0.5 | n/a | 5,791 | 41 | 0 | 0 | LO |
| Hydrophilic | 9 × 9 × 0.5 | n/a | 81,740 | 2,549 | 0 | 0 | LO |
| Cotton Gauze | 4 × 4 | n/a | 29,809 | 937 | 8 | 0 | LO |
| Telfa (non-adherent pads) | n/a | n/a | 27,884 | 2,401 | 111 | 0 | LO |
| Raytec sponges | 4 × 4 | n/a | 56,210 | 1,426 | 24 | 0 | LO |
| Lap Pad | 15 × 15 | n/a | 84,330 | 6,070 | 530 | 200 | LO |

The inventions and methods described herein can be viewed as a whole, or as a number of separate inventions, that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A biocompatible reusable medical device, comprising:
    a cellulose free laundered hydrophilic foam material, wherein the cellulose free laundered hydrophilic foam material is laundered in an aqueous solution of low particulate water to reduce manufacturing particulates such that the cellulose free laundered hydrophilic foam material has less than 10,000 particles/cm²≥5 μm, and the cellulose free laundered hydrophilic foam material has a shape having an x-dimension, y-dimension and z-dimension, wherein the cellulose free laundered hydrophilic foam material comprises an open celled reticulated foam material extending without voids throughout an internal body region of the x-dimension, y-dimension and z-dimension, wherein the cellulose free laundered hydrophilic foam material comprises a latex free material, a bisphenol A (BPA) free material, and a di(2-ethylhexyl) phthalate (DEHP) free material; and
    a plurality of spaced apart scratch resistant radiopaque ink imaging markers adhered directly on an outer surface of the open celled reticulated foam material, wherein the plurality of spaced apart scratch resistant radiopaque ink imaging markers are configured in a pattern and configured to be visible with an external imagining device at various different orientations of the biocompatible reusable medical device.

2. The biocompatible reusable medical device of claim 1, wherein the cellulose free laundered hydrophilic foam material comprises a color.

3. The biocompatible reusable medical device of claim 1, wherein the cellulose free laundered hydrophilic foam material is laundered in the aqueous solution and has a bacterial endotoxicity level below about 7.0 EU/device.

4. The biocompatible reusable medical device of claim 1, wherein the pattern comprises a grid pattern.

5. The biocompatible reusable medical device of claim 1, wherein the cellulose free laundered hydrophilic foam material comprises a bacterial endotoxin less than 20.00 EU/device.

6. The biocompatible reusable medical device of claim 1, wherein the cellulose free laundered hydrophilic foam material is non-cytotoxic.

7. The biocompatible reusable medical device of claim 1, wherein each of the plurality of spaced apart scratch resistant radiopaque ink imaging markers are arranged in a circular shape and have a diameter in a range from about 0.5 mm to about 10 mm.

8. The biocompatible reusable medical device of claim 1, wherein the pattern comprises a geometric pattern.

9. A biocompatible reusable surgical medical device, comprising:
    a hydrophilic foam material laundered in an aqueous solution of low particulate water to reduce manufacturing particulates, the hydrophilic foam material has less than 10,000 particles/cm²≥5 μm, and having a continuous voidless body region, a top surface, a bottom surface, and side surfaces, wherein the continuous voidless body region comprises an open celled structure, wherein the hydrophilic foam material comprises a cellulose free material, a latex free material, a bisphenol A (BPA) free material, and di(2-ethylhexyl) phthalate (DEHP) free material; and
    a plurality of scratch resistant radiopaque ink dot imaging markers formed in a grid pattern directly on the top surface, wherein the plurality of scratch resistant radiopaque ink dot imaging markers are configured to be visible with external imaging and each of the plurality of scratch resistant radiopaque ink dot imaging markers are spaced apart from each other, and
    wherein the biocompatible reusable surgical medical device is configured to be reused during a medical procedure.

10. The biocompatible reusable surgical medical device of claim 9, wherein the external imaging is one of x-ray imaging and ultrasound imaging.

11. The biocompatible reusable surgical medical device of claim 9, wherein each of the plurality of scratch resistant radiopaque ink dot imaging markers are arranged in a circular shape and have a diameter in a range from about 0.5 mm to about 10 mm.

12. The biocompatible reusable surgical medical device of claim 9, wherein the hydrophilic foam material comprises a color.

13. The biocompatible reusable surgical medical device of claim 9, wherein the hydrophilic foam material is sized to fit within a lumen of a trocar.

14. The biocompatible reusable surgical medical device of claim 9, wherein the hydrophilic foam material is configured to be hydrated within a sterile fluid.

15. A biocompatible reusable multi-use surgical medical device for repeated use during a medical procedure, comprising:
a laundered flexible hydrophilic foam material having a top surface, a bottom surface, and side surfaces, wherein the laundered flexible hydrophilic foam material includes a continuous open celled structure extending without voids throughout the entire flexible hydrophilic foam material, wherein the laundered flexible hydrophilic foam material is configured to be foldable into various shapes and sizes during a medical procedure, wherein the laundered flexible hydrophilic foam material is laundered in an aqueous solution of low particulate water to reduce manufacturing particulates, the laundered flexible hydrophilic foam material has less than 10,000 particles/cm$^2$≥5 µm, and, wherein the laundered flexible hydrophilic foam material comprises a cellulose free material, a latex free material, a bisphenol A (BPA) free material, and a di(2-ethylhexyl) phthalate (DEHP) free material; and
a plurality of spaced apart scratch resistant radiopaque ink imaging markers arranged in a grid pattern directly on the top surface of the laundered flexible hydrophilic foam material, wherein at least a portion of the plurality of spaced apart scratch resistant radiopaque ink imaging markers are configured to be visible with external imaging at different spatial orientations and each of the plurality of spaced apart scratch resistant radiopaque ink imaging markers have a width in a range from about 0.5 mm to about 2 mm.

16. The biocompatible reusable multi-use surgical medical device of claim 15, wherein the laundered flexible hydrophilic foam material comprises a color.

17. The biocompatible reusable multi-use surgical medical device of claim 15, wherein the laundered flexible hydrophilic foam material is sized to fit within a lumen of a trocar.

18. The biocompatible reusable multi-use surgical medical device of claim 15, wherein the laundered flexible hydrophilic foam material is configured to be hydrated with a sterile fluid and configured to be wrung out to remove at least some of the sterile fluid, and configured to be wrung out with the sterile fluid during the medical procedure to remove at least some blood and bodily fluids it may have absorbed and configured to be reused to absorb additional blood and bodily fluids.

19. The biocompatible reusable multi-use surgical medical device of claim 15, wherein the laundered flexible hydrophilic foam material comprises a bacterial endotoxin less than 20.00 EU/device.

20. The biocompatible reusable medical device of claim 1, wherein the cellulose free laundered hydrophilic foam material is configured to be hydrated with a sterile fluid and configured to be wrung out to remove at least some of the sterile fluid, and configured to be wrung out with the sterile fluid during a medical procedure to remove at least some blood or bodily fluids it may have absorbed and configured to be reused to absorb additional blood or bodily fluids during the medical procedure.

21. The biocompatible reusable surgical medical device of claim 9, wherein the hydrophilic foam material is configured to be hydrated with a sterile fluid and configured to be wrung out to remove at least some of the sterile fluid, and configured to be wrung out with the sterile fluid during the medical procedure to remove at least some blood or bodily fluids it may have absorbed and configured to be reused to absorb additional blood or bodily fluids during the medical procedure.

* * * * *

UNITED STATES PATENT AND TRADEMARK OFFICE
CERTIFICATE OF CORRECTION

| | | |
|---|---|---|
| PATENT NO. | : 12,419,988 B2 | Page 1 of 1 |
| APPLICATION NO. | : 17/063484 | |
| DATED | : September 23, 2025 | |
| INVENTOR(S) | : Norman C. Furbush | |

It is certified that error appears in the above-identified patent and that said Letters Patent is hereby corrected as shown below:

In the Claims

Column 29, Claim 14, Line 9: "WITHIN" should be changed to --WITH--

Signed and Sealed this
Eleventh Day of November, 2025

John A. Squires
*Director of the United States Patent and Trademark Office*